United States Patent
Ye et al.

(10) Patent No.: US 10,654,797 B2
(45) Date of Patent: May 19, 2020

(54) SOLID FORMS OF AN ADAMANTYL COMPOUND, COMPOSITIONS AND USES THEREOF

(71) Applicant: NORTH & SOUTH BROTHER PHARMACY INVESTMENT COMPANY LIMITED, Hong Kong (CN)

(72) Inventors: Huiqing Ye, Guangdong (CN); Jinchao Xu, Guangdong (CN); Bifei He, Guangdong (CN); Guangyuan Liu, Guangdong (CN); Yuping Fan, Guangdong (CN); Zhongqing Wang, Guangdong (CN); Zhonghua Luo, Guangdong (CN)

(73) Assignee: North & South Brother Pharmacy Investment Company Limited, Hong Kong (CN)

( * ) Notice: Subject to any disclaimer, the term of this patent is extended or adjusted under 35 U.S.C. 154(b) by 0 days.

(21) Appl. No.: 16/343,165

(22) PCT Filed: Nov. 2, 2017

(86) PCT No.: PCT/CN2017/109055
§ 371 (c)(1),
(2) Date: Apr. 18, 2019

(87) PCT Pub. No.: WO2018/082596
PCT Pub. Date: May 11, 2018

(65) Prior Publication Data
US 2019/0315679 A1     Oct. 17, 2019

(30) Foreign Application Priority Data

Nov. 3, 2016   (CN) .......................... 2016 1 0958199

(51) Int. Cl.
| | |
|---|---|
| *C07C 271/24* | (2006.01) |
| *A61K 31/27* | (2006.01) |
| *A61K 31/445* | (2006.01) |
| *A61K 31/473* | (2006.01) |
| *A61K 31/55* | (2006.01) |

(52) U.S. Cl.
CPC ............ *C07C 271/24* (2013.01); *A61K 31/27* (2013.01); *A61K 31/445* (2013.01); *A61K 31/473* (2013.01); *A61K 31/55* (2013.01); *C07B 2200/13* (2013.01)

(58) Field of Classification Search
CPC .... A61K 31/27; A61K 31/445; A61K 31/473; A61K 31/55; C07B 2200/13; C07C 271/24
USPC ......................................................... 514/479
See application file for complete search history.

(56) References Cited

FOREIGN PATENT DOCUMENTS

| WO | WO 2000/075127 | 12/2000 |
|---|---|---|
| WO | WO 2008/025539 | 3/2008 |
| WO | WO 2008/025540 | 3/2008 |
| WO | WO 2008/157270 | 12/2008 |
| WO | WO 2009/005998 | 1/2009 |
| WO | WO 2016/127924 | 8/2016 |

OTHER PUBLICATIONS

International Search Report and Written Opinion of PCT/CN2017/109055 dated Jan. 19, 2018 (9 pages).

*Primary Examiner* — Kristin A Vajda
(74) *Attorney, Agent, or Firm* — Sheppard Mullin Richter & Hampton LLP

(57) ABSTRACT

Provided herein are crystalline forms of (((((1r, 3R, 5S, 7r)-3, 5-dimethyladamantan-1-yl)carbamoyl) oxy) methyl benzoate (Compound (I)): Also provided are compositions comprising the crystalline forms of Compound (I), processes of manufacture and methods of using the crystalline forms of Compound (I).

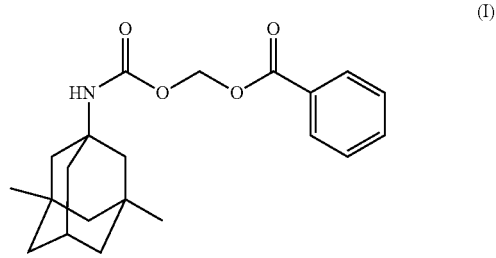

(I)

18 Claims, 3 Drawing Sheets

SOLID FORMS OF AN ADAMANTYL COMPOUND, COMPOSITIONS AND USES THEREOF

CROSS REFERENCE TO RELATED APPLICATIONS

The present application is a national stage application of International Application PCT/CN2017/109055, filed Nov. 2, 2017, which claim priority of Chinese Patent Application No. 201610958199.8, filed Nov. 3, 2016, the contents of which are incorporated by reference in their entireties into the present disclosure.

FIELD

The present disclosure relates to crystalline forms of ((((1r,3R,5S,7r)-3,5-dimethyladamantan-1-yl)carbamoyl)oxy)methyl benzoate, processes for preparing the crystalline forms, and pharmaceutical compositions comprising the crystalline forms, and use of the crystalline forms or pharmaceutical compositions in the treatment of diseases of the central nervous system.

BACKGROUND

Many neurodegenerative diseases occur as a result of the neurodegenerative processes. Neurodegeneration is the progressive loss of structure or function of neurons, including death of neurons. Neurodegenerative diseases are hardly curable, resulting in progressive degeneration and/or death of neuron cells.

Memantine is an N-methyl-D-aspartate (NMDA) receptor antagonist, and it reduces certain types of brain activity by binding to NMDA receptors on brain cells and blocking the activity of the neurotransmitter glutamate. Memantine has been shown to have therapeutic effects on moderate-to-severe Alzheimer's disease and in dementia with Lewy bodies. It has also been demonstrated that memantine has efficacy in treating various diabetic diseases or conditions. The structure of memantine is shown as follows:

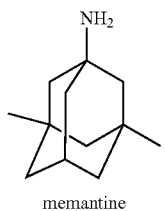

memantine

However, memantine has certain physical and chemical properties that limit its therapeutic use. For instance, memantine has fairly high water solubility which presents challenges for drug formulation. In addition, the use of memantine is associated with adverse effects such as confusion, dizziness, drowsiness, headache, insomnia, agitation, and hallucinations.

SUMMARY

Below is a non-limiting summary of several aspects of the present disclosure. These and other aspects will be more completely described in other sections.

The present disclosure provides crystalline forms of a memantine derivative with more desirable properties, such as solubility, useful in treating a central nervous system disease in a subject. The present disclosure further provides methods of preparing the crystalline forms, use of the crystalline forms in the treatment of a central nervous system disease in a subject, in particular a central nervous system disease in a human, and compositions comprising the crystalline forms.

In one aspect, disclosed herein are crystalline forms of ((((1r,3R,5S,7r)-3,5-dimethyladamantan-1-yl)carbamoyl)oxy)methyl benzoate (Compound (I)) having the formula:

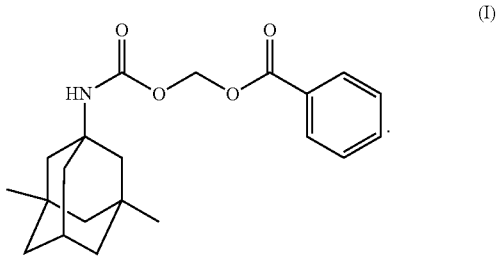 [SMILES: CC12CC3CC(C)(C1)CC(NC(=O)OCOC(=O)c1ccccc1)(C3)C2]

In one aspect, provided herein is a crystalline form of Compound (I).

In some embodiments, provided herein is a crystalline form of Compound (I) selected from
- crystalline Form I characterized by an X-ray powder diffraction pattern comprising at least three peaks selected from the peaks expressed as 2θ at 7.7±0.2°, 8.9±0.2°, 10.7±0.2°, 13.1±0.2°, 14.2±0.2°, 15.4±0.2°, 18.0±0.2°, 18.7±0.2°, 21.4±0.2°, 21.6±0.2°, 22.4±0.2°, 22.8±0.2°, 23.9±0.2°, 25.5±0.2°, 26.5±0.2°, and 27.0±0.2°, and
- crystalline Form II characterized by an X-ray powder diffraction pattern comprising at least three peaks selected from the peaks expressed as 2θ at 9.6±0.20, 13.8±0.2°, 14.7±0.2°, 15.0±0.2°, 16.1±0.2°, 16.8±0.2°, 17.8±0.2°, 18.5±0.2°, 19.0±0.2°, 19.4±0.2°, 20.4±0.2°, 21.7±0.2° and 22.6±0.2°.

In some embodiments, provided herein is a crystalline form of Compound (I) selected from
- crystalline Form I characterized by an X-ray powder diffraction pattern comprising at least three peaks selected from the peaks expressed as 2θ at 14.2±0.2°, 15.4±0.2°, 17.96±0.2°, 18.7±0.2°, 21.4±0.2°, 21.6±0.20 and 22.4±0.2°, and
- crystalline Form II characterized by an X-ray powder diffraction pattern comprising at least three peaks selected from the peaks expressed as 2θ at 13.8±0.2°, 14.7±0.2°, 15.0±0.2°, 16.1±0.2°, 16.8±0.2°, 18.5±0.2°, 19.4±0.2°, 21.7±0.2° and 22.6±0.2°.

In some embodiments, provided herein is a crystalline form of Compound (I) selected from
- crystalline Form I characterized by an X-ray powder diffraction pattern comprising at least three peaks selected from the peaks expressed as 2θ at 14.17±0.20, 15.43±0.2°, 17.96±0.2°, 18.74±0.2°, 21.40±0.2°, 21.55±0.2° and 22.36±0.2°, and
- crystalline Form II characterized by an X-ray powder diffraction pattern comprising at least three peaks selected from the peaks expressed as 2θ at 13.75±0.2°, 14.70±0.2°, 14.99±0.2°, 16.11±0.2°, 16.78±0.2°, 18.50±0.2°, 19.42±0.2°, 21.66±0.20 and 22.63±0.2°.

In some embodiments, the crystalline form exists in substantially anhydrous form.

In some embodiments, provided herein is a crystalline Form I of Compound (I) characterized by an X-ray powder diffraction pattern comprising at least three peaks selected from the peaks expressed as 2θ at 14.17±0.2°, 15.43±0.2°, 17.96±0.2°, 18.74±0.2°, 21.40±0.2°, 21.55±0.20 and 22.36±0.2°.

In some embodiments, provided herein is a crystalline Form I of Compound (I) characterized by an X-ray powder diffraction pattern comprising peaks expressed as 2θ at 14.17±0.2°, 15.43±0.2°, 17.96±0.2°, 18.74±0.2°, 21.40±0.2°, 21.55±0.20 and 22.36±0.2°.

In some embodiments, provided herein is a crystalline Form I of Compound (I) characterized by an X-ray powder diffraction pattern comprising peaks expressed as 2θ at 7.68±0.2°, 8.88±0.2°, 14.17±0.2°, 15.43±0.2°, 16.73±0.2°, 17.65±0.2°, 17.96±0.2°, 18.74±0.2°, 19.16±0.2°, 21.40±0.2°, 21.55±0.2°, 22.36±0.2°, and 22.81±0.2°.

In some embodiments, provided herein is a crystalline Form I of Compound (I) having an X-ray powder diffraction (XRPD) pattern substantially as shown in FIG. 1.

In some embodiments, provided herein is a crystalline form I of Compound (I) characterized by a differential scanning calorimetry thermogram comprising an endothermic peak at 91.55° C.±2° C.

In some embodiments, provided herein is a crystalline Form I of Compound (I) having a differential scanning calorimetry thermogram substantially as shown in FIG. 2.

In some embodiments, provided herein is a crystalline Form I of Compound (I) having a thermogravimetric analysis curve substantially as shown in FIG. 3.

In some embodiments, provided herein is a crystalline Form II of Compound (I) characterized by an X-ray powder diffraction pattern comprising at least three peaks selected from the peaks expressed as 2θ at 13.75±0.2°, 14.70±0.2°, 14.99±0.2°, 16.11±0.2°, 16.78±0.2°, 18.50±0.2°, 19.42±0.2°, 21.66±0.2° and 22.63±0.2°.

In some embodiments, provided herein is a crystalline Form II of Compound (I) characterized by an X-ray powder diffraction pattern comprising at least three peaks selected from the peaks expressed as 2θ at 13.75±0.2°, 14.70±0.2°, 14.99±0.2°, 16.11±0.2°, 16.78±0.2°, 18.50±0.2°, 19.42±0.2°, 21.66±0.2° and 22.63±0.2°.

In some embodiments, provided herein is a crystalline Form II of Compound (I) characterized by an X-ray powder diffraction pattern comprising peaks expressed as 2θ at 9.61±0.2°, 13.75±0.2°, 14.70±0.2°, 14.99±0.2°, 16.11±0.2°, 16.78±0.2°, 17.81±0.2°, 18.50±0.2°, 18.97±0.2°, 19.42±0.2°, 20.43±0.2°, 21.66±0.2°, 22.63±0.2°, 23.19±0.20, 24.47±0.20°.

In some embodiments, provided herein is a crystalline Form II of Compound (I) having an X-ray powder diffraction (XRPD) pattern substantially as shown in FIG. 4.

In some embodiments, provided herein is a crystalline Form II of Compound (I) characterized by a differential scanning calorimetry thermogram comprising an endothermic peak at 80.53° C.±2° C.

In some embodiments, provided herein is a crystalline Form II of Compound (I) having a differential scanning calorimetry thermogram substantially as shown in FIG. 5.

In some embodiments, provided herein is a crystalline Form II of Compound (I) having a thermogravimetric analysis curve substantially as shown in FIG. 6.

In another aspect, provided is pharmaceutical composition comprising a crystalline form, such as crystalline Form I or II, of Compound (I) or a combination thereof, and a pharmaceutically acceptable excipient. In some embodiments, the pharmaceutical composition further comprises a cholinesterase inhibitor. In some embodiments, the cholinesterase inhibitor is tacrine, donepezil, huperzine-A, galanthamine, rivastigmine, or a combination thereof.

In another aspect, provided is a method of preventing, treating or lessening a central nervous system disease, a neurodegenerative disease, or a symptom of diabetes in a subject in need thereof comprising administering to the subject a therapeutically effective amount of a crystalline form, such as crystalline Form I or II, of Compound (I) or the pharmaceutical composition thereof.

In another aspect, provided is use of a crystalline form, such as crystalline Form I or II, of Compound (I) or the pharmaceutical composition thereof in the manufacture of a medicament for preventing, treating or lessening a central nervous system disease, a neurodegenerative disease, or a symptom of diabetes in a subject.

In some embodiments, the central nervous system disease is Parkinson syndrome, Alzheimer's disease, Huntington's disease, atrophic myelitis, AIDS dementia, vascular dementia, seizures, neuralgia, or abstinence symptoms.

DETAILED DESCRIPTION

Figure 1:
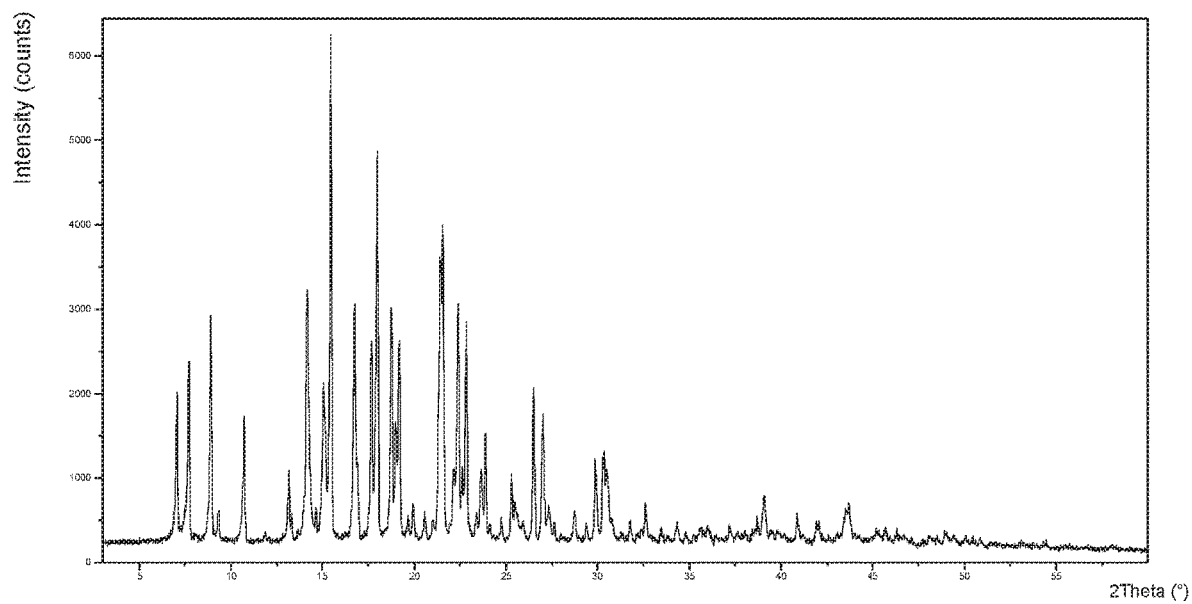
FIG. 1 shows an X-ray powder diffraction (XRPD) pattern of crystalline Form I of Compound (I).

The compound, (((((1r,3R,5S,7r)-3,5-dimethyladamantan-1-yl)carbamoyl)oxy)methyl benzoate, designated herein as Compound (I), has the following formula:

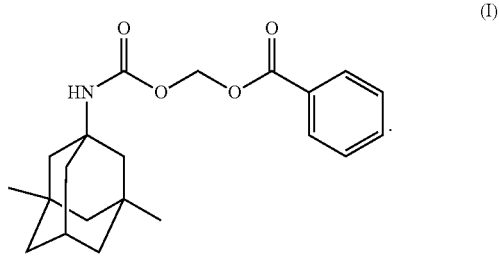 [SMILES: CC12CC3CC(C)(C1)CC(NC(=O)OCOC(=O)c1ccccc1)(C3)C2]

Compound (I) is a memantine derivative, and slowly releases memantine in vivo. Disclosed herein are crystalline forms of Compound (I).

Definitions

Some embodiments of the present disclosure are described in detail, and examples are illustrated by accompanying structural or chemical formulas. The present disclosure is intended to encompass all alternatives, modifications, and equivalent technology that are within the scope of the technology as defined in the claims. Persons skilled in the art in the relevant field should recognize that many methods and materials that are similar or equivalent to those described herein can be used to practice the technology. The present technology is not limited to the methods and materials described herein. If one or more sections (including but not limited to the a definition of a terminology, application of a terminology, and techniques described, etc.) of any literature, patent and similar materials are different or in conflict with the present disclosure, the present disclosure shall prevail. All patents and publications referred to herein are incorporated by reference in their entirety.

Unless otherwise noted, all technical terms used herein have the same meaning as those commonly understood by persons skilled in the art of the relevant field.

The term "comprise" and variations thereof, such as, "comprises" and "comprising" are to be construed in an open, inclusive sense, that is, as "including, but not limited to." The term "consisting essentially of" when used to define compositions and methods, shall mean excluding other elements of any essential significance to the compositions or methods. For example, a composition consisting essentially of the elements as defined herein would not exclude other elements that do not materially affect the basic and novel characteristic(s) of the claimed invention. The term "consisting of" shall mean excluding more than trace amount of other ingredients and substantial method steps recited. Embodiments defined by each of these transition terms are within the scope of this disclosure.

The singular forms "a," "an," and "the" include plural references unless the context clearly dictates otherwise. For example, reference to "the excipient" includes a plurality of such excipients.

Recitation of numeric ranges of values throughout the disclosure is intended to serve as a shorthand notation of referring individually to each separate value falling within the range inclusive of the values defining the range, and each separate value is incorporated in the specification as it were individually recited herein.

The term "about" includes the indicated amount±1%, ±2%, ±3%, ±4%, ±5%, ±6%, ±7%, ±8%, ±9%, ±10%, ±15% or 20%. In certain embodiments, the term "about" includes the indicated amount±10%. In other embodiments, the term "about" includes the indicated amount±5%. In certain other embodiments, the term "about" includes the indicated amount±1%. The term "about X" also includes "X".

The term "2θ value" or "2θ" refers to the peak position measured in degrees (°) by an X-ray diffraction instrument and the common horizontal axis of the X-ray diffraction spectrum. The experimental setting requires that when the incident beam and a certain crystal surface form an angle θ (θ), if the reflection is diffracted, the reflected beam be recorded in 2θ (2θ) angle. It should be understood that the specific 2θ value of a crystalline polymorph is intended to refer to the 2θ value (in degrees) measured using the X-ray diffraction experimental conditions described herein. For example, as described herein, the use of radiation sources (Cu, Kα, Kα1 (Å): 1.540598; kα2 (Å): 1.544426; kα2/kα1 strength ratio: 0.50).

The term "X-ray powder diffraction" pattern or "XRPD" pattern refers to the observed diffraction spectra or the parameters derived from it. Characterization of X-ray powder diffraction patterns are characterized by peak position (abscissa) and peak intensity (ordinate). The relative peak heights of the XRPD spectra depend on many factors related to sample preparation and instrument geometry, while the peak positions are relatively insensitive to the experimental details. Thus, in some embodiments, the crystalline forms of the present disclosure are characterized by an XRPD pattern with certain peak positions substantially the same as those of the XRPD pattern provided in the drawings herein. According to the conditions of the instrument used herein, the diffraction peaks has a margin of error of ±0.10, ±0.2°, ±0.3°, ±0.4° or ±0.5°, and in some embodiments the margin of error of the diffraction peaks is ±0.2°.

The peak height of the DSC curve depends on many factors related to sample preparation and instrument geometry, while the peak position is relatively insensitive to the experimental details. Thus, in some embodiments, the crystalline forms of the present disclosure are characterized by a DSC diagram having a characteristic peak position substantially the same as that of the DSC diagram provided in the drawings herein. According to the instrument conditions used herein, the melting peak has a margin of error of ±1° C., ±2° C., ±3° C., ±4° C. or ±5° C. In some embodiments, the melting peak has a margin of error of ±2° C.

The term relative intensity refers to the ratio of the intensity of a peak to the intensity of the strongest peak when the intensity of the strongest peak in the X-ray powder diffraction (XRPD) pattern is 100%.

When referring to a spectrum and/or data appearing in the spectrum, a person skilled in the art of the relevant field will recognize that the term "peak" does not refer to background noise.

The term "substantially the same" refers to two diagrams having corresponding characteristic peaks at positions that are within the margin of error described herein. In some embodiments, characteristic peaks are those having a relative intensity of about 5% or more. In some embodiments, characteristic peaks are those that have a relative intensity of about 10% or more. In some embodiments, characteristic peaks are those that have a relative intensity of about 25% or more.

The term "anhydrous form" refers to a crystalline form that does not have water bound in the crystal lattice. However, the crystals may contain trace amount of water or other solvents not bound in the crystal lattice.

As used herein, the term "treatment" or "treating" any disease or disease refers to providing beneficial or desired clinical results, which may include in some embodiments, slowing or preventing or alleviating the disease or at least one of its clinical symptoms. In some embodiments, "treatment" or "treating" refers to the relaxation or improvement of at least one body parameter, including body parameters that may not be perceived by the patient. In some embodiments, "treatment" or "treating" refers to the adjustment of a disease or condition from the body (e.g., stabilizing perceptible symptoms) or physiology (e.g., stabilizing body parameters) or the above two aspects. In other embodiments, "treatment" or "treating" means preventing or delaying the onset, occurrence, or deterioration of a disease or a symptom.

The term "effective amount" or "therapeutically effective amount" refers to the amount sufficient to provide a desired biological or medical response or benefit. The response includes improving or relieving a disease, eliminating or reducing one or more symptoms of the disease, or slowing the onset or progression of a disease, preventing or delaying relapse or recurrence of a previously diagnosed or treated disease, and/or preventing or delaying the onset of a disease.

The term "subject" refers to an animal, such as a mammal, including both humans and non-humans. In some embodiments, the subject is a human.

The term "composition" when referring to a mixture of a crystalline form and its tautomer means that the purity of the crystalline form relative to its tautomer is at least 60%, or at least 70%, or at least 80%, or at least 85%, or at least 90%, or at least 93%, or at least 95%, or at least 98%, or at least 99% or, at least 99.5%, or at least 99.6%, or at least 99.7%, or at least 99.8%, or at least 99.9%; or when referring to a mixture of a first crystalline form and one or more other crystalline forms, means that the purity of the first crystalline form relative to the other one or more crystalline forms is at least 60%, or at least 70%, or at least 80%, or at least 85%, or at least 90%, or at least 93%, or at least 95%, or at least 98%, or at least 99%, or at least 99.5%, or at least 99.6%, or at least 99.7%, or at least 99.8%, or at least 99.9%; or the total volume or weight of other crystalline forms is less than 20%, or less than 10%, or less than 5%, or less than 3%, or less than 1%, or less than 0.5%, or less than 0.1%, or less than 0.01% of the total volume of weight of all crystalline forms.

In some embodiments, the crystalline form of the Compound (I) is present in substantially pure crystalline form.

The purity of the crystalline forms disclosed herein can be determined by, for example, known methods such as X-ray powder diffraction, thermal analysis, etc. The purity of a crystalline form or a mixture of crystalline forms need not be 100%. In some embodiments, the purity is not less than 70%. In some embodiments, the purity is not less than 80%. In some embodiments, the purity is not less than 90%. In some embodiments, the purity is not less than 95%. In some embodiments, the purity is not less than 98%.

In addition, abbreviations as used herein have respective meanings as follows:

| | |
|---|---|
| μL | microliter |
| μm | micrometer |
| CH$_3$CN | acetonitrile |
| g | gram |
| HCl | hydrochloride |
| LC/MS | liquid chromatography-mass spectrometry |
| M | molar |
| mg | milligram |
| min | minute |
| mL | milliliter |
| mM | millimolar |
| mmol | millimole |
| nm | nanometer |
| NMR | nuclear magnetic resonance |
| ppm | part(s) per million |
| RH | relative humidity |

Crystalline Forms of Compound (I)

Exemplary techniques for characterizing crystalline forms are described herein. These techniques may be used individually or in combination to characterize the crystalline forms. The crystalline pattern may also be referenced by the features of the drawings disclosed herein. The different crystalline forms of the same compound can have an impact on one or more physical properties, such as stability, solubility, melting point, bulk density, flow properties, bioavailability, low hygroscopicity, etc.

This present disclosure provides crystalline forms of a memantine derivative with more desirable properties, such as solubility. Disclosed herein are crystalline forms of ((((1r,3R,5S,7r)-3,5-dimethyladamantan-1-yl)carbamoyl)oxy)methyl benzoate (Compound (I)) having the formula:

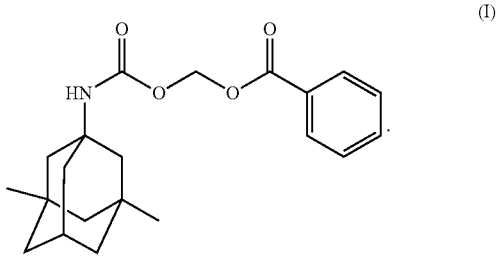 [SMILES: CC12CC3CC(C)(C1)CC(NC(=O)OCOC(=O)c1ccccc1)(C3)C2]

In some embodiments, provided herein is a crystalline form of Compound (I) selected from
crystalline Form I characterized by an X-ray powder diffraction pattern comprising at least three peaks selected from the peaks expressed as 2θ at 7.7±0.2°, 8.9±0.2°, 10.7±0.2°, 13.1±0.2°, 15.4±0.2°, 18.0±0.2°, 21.6±0.2°, 22.8±0.2°, 23.9±0.2°, 25.5±0.2°, 26.5±0.2°, and 27.0±0.2°, and
crystalline Form II characterized by an X-ray powder diffraction pattern comprising at least three peaks selected from the peaks expressed as 2θ at 9.6±0.20, 13.8±0.2°, 14.7±0.2°, 15.0±0.2°, 16.1±0.2°, 16.8±0.2°, 17.8±0.2°, 18.5±0.2°, 19.0±0.2°, 19.4±0.2°, 20.4±0.2°, and 21.7±0.2°.

In some embodiments, provided herein is a crystalline form of Compound (I) selected from
crystalline Form I characterized by an X-ray powder diffraction pattern comprising at least three peaks selected from the peaks expressed as 2θ at 14.2±0.2°, 15.4±0.2°, 17.96±0.2°, 18.7±0.2°, 21.4±0.2°, 21.6±0.20 and 22.4±0.2°, and
crystalline Form II characterized by an X-ray powder diffraction pattern comprising at least three peaks selected from the peaks expressed as 2θ at 13.8±0.2°, 14.7±0.2°, 15.0±0.2°, 16.1±0.2°, 16.8±0.2°, 18.5±0.2°, 19.4±0.2°, 21.7±0.2° and 22.6±0.2°.

In some embodiments, provided herein is a crystalline form of Compound (I) selected from
crystalline Form I characterized by an X-ray powder diffraction pattern comprising at least three peaks selected from the peaks expressed as 2θ at 14.17±0.20, 15.43±0.2°, 17.96±0.2°, 18.74±0.2°, 21.40±0.2°, 21.55±0.20 and 22.36±0.2°, and
crystalline Form II characterized by an X-ray powder diffraction pattern comprising at least three peaks selected from the peaks expressed as 2θ at 13.75±0.2°, 14.70±0.2°, 14.99±0.2°, 16.11±0.2°, 16.78±0.2°, 18.50±0.2°, 19.42±0.2°, 21.66±0.2° and 22.63±0.2°.

In some embodiments, the crystalline form exists in substantially anhydrous form.

In some embodiments, provided herein is a crystalline Form I of Compound (I) characterized by an X-ray powder diffraction pattern comprising at least three peaks selected from the peaks expressed as 2θ at 7.7±0.2°, 8.9±0.2°, 10.7±0.2°, 13.1±0.2°, 15.4±0.2°, 18.0±0.2°, 21.6±0.2°, 22.8±0.2°, 23.9±0.2°, 25.5±0.2°, 26.5±0.2°, and 27.0±0.2°.

In some embodiments, provided herein is a crystalline Form I of Compound (I) characterized by an X-ray powder diffraction pattern comprising at least three peaks expressed as 2θ selected from the groups: (A) 7.7±0.2°, 8.9±0.2°, and 10.7±0.2°; (B) 13.1±0.2°, 15.4±0.2°, and 18.0±0.2°; (C) 21.6±0.2°, 22.8±0.2°, and 23.9±0.2°; and (D) 25.5±0.20, 26.5±0.20, and 27.0±0.2°.

In some embodiments, provided herein is a crystalline Form I of Compound (I) characterized by an X-ray powder diffraction pattern comprising peaks expressed as 2θ at 7.7±0.2°, 8.9±0.2°, and 10.7±0.2°.

In some embodiments, provided herein is a crystalline Form I of Compound (I) characterized by an X-ray powder diffraction pattern comprising peaks expressed as 2θ at 13.1±0.2°, 15.4±0.2°, and 18.0±0.2°.

In some embodiments, provided herein is a crystalline Form I of Compound (I) characterized by an X-ray powder diffraction pattern comprising peaks expressed as 2θ at 21.6±0.2°, 22.8±0.2°, and 23.9±0.2°.

In some embodiments, provided herein is a crystalline Form I of Compound (I) characterized by an X-ray powder diffraction pattern comprising peaks expressed as 2θ at 25.5±0.2°, 26.5±0.2°, and 27.0±0.2°.

In some embodiments, provided herein is a crystalline Form I of Compound (I) characterized by an X-ray powder diffraction pattern comprising at least three peaks selected from the peaks expressed as 2θ at 14.2±0.2°, 15.4±0.2°, 18.0±0.2°, 18.7±0.2°, 21.4±0.2°, 21.6±0.2° and 22.4±0.2°.

In some embodiments, provided herein is a crystalline Form I of Compound (I) characterized by an X-ray powder diffraction pattern comprising at least three peaks selected from the peaks expressed as 2θ at 14.17±0.2°, 15.43±0.2°, 17.96±0.2°, 18.74±0.2°, 21.40±0.2°, 21.55±0.2° and 22.36±0.2°.

In some embodiments, provided herein is a crystalline Form I of Compound (I) characterized by an X-ray powder diffraction pattern comprising at least three peaks selected from the peaks expressed as 2θ at 14.2±0.10, 15.4±0.10, 18.0±0.10, 18.7±0.10, 21.4±0.10, 21.6±0.1° and 22.4±0.1°.

In some embodiments, provided herein is a crystalline Form I of Compound (I) characterized by an X-ray powder diffraction pattern comprising at least three peaks selected from the peaks expressed as 2θ at 14.17±0.10, 15.43±0.10, 17.96±0.10, 18.74±0.10, 21.40±0.10, 21.55±0.10 and 22.36±0.10°.

In some embodiments, provided herein is a crystalline Form I of Compound (I) characterized by an X-ray powder diffraction pattern comprising peaks expressed as 2θ at 14.2±0.2°, 15.4±0.2°, 18.0±0.2°, 18.7±0.2°, 21.4±0.2°, 21.6±0.20 and 22.4±0.2°.

In some embodiments, provided herein is a crystalline Form I of Compound (I) characterized by an X-ray powder diffraction pattern comprising peaks expressed as 2θ at 14.17±0.2°, 15.43±0.2°, 17.96±0.2°, 18.74±0.2°, 21.40±0.2°, 21.55±0.20 and 22.36±0.2°.

In some embodiments, provided herein is a crystalline Form I of Compound (I) characterized by an X-ray powder diffraction pattern comprising peaks expressed as 2θ at 14.2±0.10, 15.4±0.10, 18.0±0.10, 18.7±0.1°, 21.4±0.1°, 21.6±0.10 and 22.4±0.1°.

In some embodiments, provided herein is a crystalline Form I of Compound (I) characterized by an X-ray powder diffraction pattern comprising peaks expressed as 2θ at 7.7±0.2°, 8.9±0.2°, 14.2±0.2°, 15.4±0.2°, 16.7±0.2°, 17.7±0.2°, 18.0±0.2°, 18.7±0.2°, 19.2±0.20, 21.4±0.20, 21.6±0.20, 22.4±0.20, and 22.8±0.2°.

In some embodiments, provided herein is a crystalline Form I of Compound (I) characterized by an X-ray powder diffraction pattern comprising peaks expressed as 2θ at 7.68±0.2°, 8.88±0.2°, 14.17±0.2°, 15.43±0.2°, 16.73±0.2°, 17.65±0.2°, 17.96±0.2°, 18.74±0.2°, 19.16±0.2°, 21.40±0.2°, 21.55±0.2°, 22.36±0.2°, and 22.81±0.2°.

In some embodiments, provided herein is a crystalline Form I of Compound (I) having an X-ray powder diffraction (XRPD) pattern substantially as shown in FIG. 1.

In some embodiments, provided herein is a crystalline Form I of Compound (I) characterized by a differential scanning calorimetry thermogram comprising an endothermic peak at 91.55° C.±2° C.

In some embodiments, provided herein is a crystalline Form I of Compound (I) characterized by a differential scanning calorimetry (DSC) having a melting endothermic peak at 85-95° C., a temperature with maximum endotherm of 91.55° C., and the melting enthalpy is about 86.56 J/G, when measured using a DSC heating rate of 10° C./min.

Figure 2:
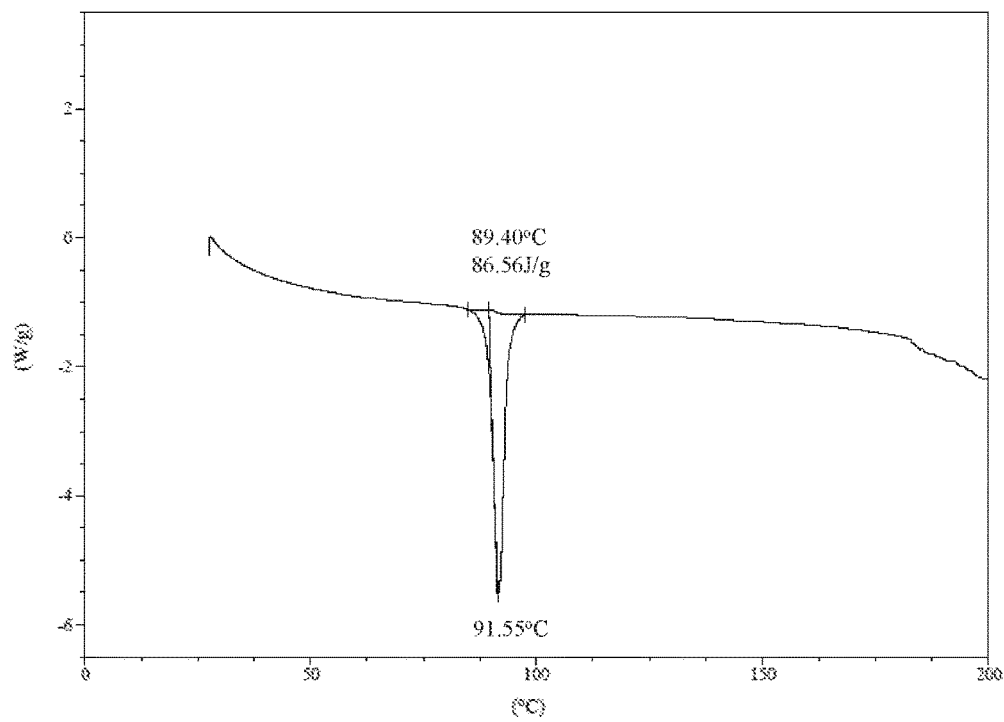
FIG. 2 shows a differential scanning calorimetry (DSC) thermogram of crystalline Form I of Compound (I).

In some embodiments, provided herein is a crystalline Form I of Compound (I) having a differential scanning calorimetry thermogram substantially as shown in FIG. 2.

In some embodiments, provided herein is a crystalline Form I of Compound (I) having a thermogravimetric analysis (TGA) with no significant weight loss before the 150° C. temperature before the degradation process begins. The detected weight loss from 25° C. to 150° C. is less than 0.21 wt % and equivalent to dry loss, which confirms that crystalline Form I does not contain a large amount of residual solvents, including water.

Figure 3:
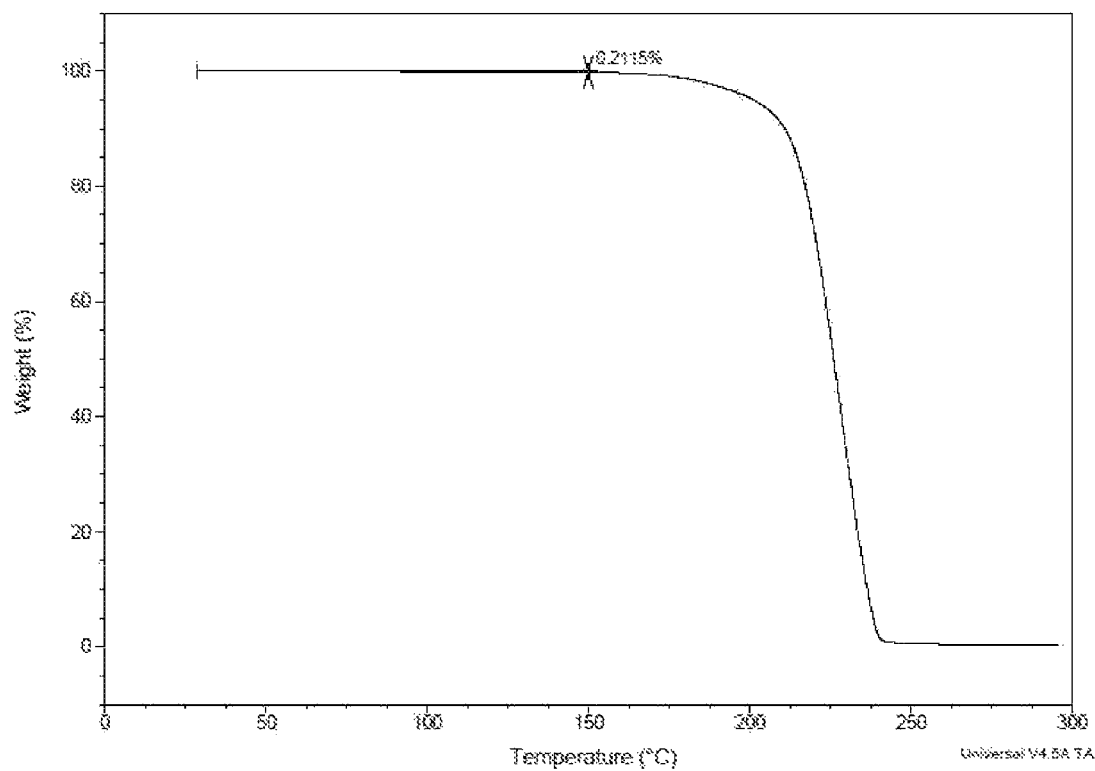
FIG. 3 shows a thermogravimetric analysis (TGA) curve of crystalline Form I of Compound (I).

In some embodiments, provided herein is a crystalline Form I of Compound (I) having a thermogravimetric analysis curve substantially as shown in FIG. 3.

Two or more features of crystalline Form I of Compound (I) may be combined.

In some embodiments, provided herein is a crystalline Form II of Compound (I) characterized by an X-ray powder diffraction pattern comprising at least three peaks selected from the peaks expressed as 2θ at 9.6±0.20, 13.8±0.2°, 14.7±0.2°, 15.0±0.2°, 16.1±0.2°, 16.8±0.2°, 17.8±0.2°, 18.5±0.2°, 19.0±0.2°, 19.4±0.2°, 20.4±0.2°, and 21.7±0.2°.

In some embodiments, provided herein is a crystalline Form II of Compound (I) characterized by an X-ray powder diffraction pattern comprising at least three peaks expressed as 2θ selected from the groups: (A) 9.6±0.2°, 13.8±0.2°, and 14.7±0.2°; (B) 15.0±0.2°, 16.1±0.2°, and 16.8±0.2°; (C) 17.8±0.2°, 18.5±0.2°, and 19.0±0.2°; and (D) 19.4±0.2°, 20.4±0.2°, and 21.7±0.2°.

In some embodiments, provided herein is a crystalline Form II of Compound (I) characterized by an X-ray powder diffraction pattern comprising peaks expressed as 2θ at 9.6±0.2°, 13.8±0.2°, and 14.7±0.2°.

In some embodiments, provided herein is a crystalline Form II of Compound (I) characterized by an X-ray powder diffraction pattern comprising peaks expressed as 2θ at 15.0±0.2°, 16.1±0.2°, and 16.8±0.2°.

In some embodiments, provided herein is a crystalline Form II of Compound (I) characterized by an X-ray powder diffraction pattern comprising peaks expressed as 2θ at 17.8±0.2°, 18.5±0.2°, and 19.0±0.2°.

In some embodiments, provided herein is a crystalline Form II of Compound (I) characterized by an X-ray powder diffraction pattern comprising peaks expressed as 2θ at 19.4±0.2°, 20.4±0.2°, and 21.7±0.2°.

In some embodiments, provided herein is a crystalline Form II of Compound (I) characterized by an X-ray powder diffraction pattern comprising at least three peaks selected from the peaks expressed as 2θ at 13.8±0.2°, 14.7±0.2°, 15.0±0.2°, 16.1±0.2°, 16.8±0.2°, 18.5±0.2°, 19.4±0.2°, 21.7±0.2° and 22.6±0.2°.

In some embodiments, provided herein is a crystalline Form II of Compound (I) characterized by an X-ray powder diffraction pattern comprising at least three peaks selected from the peaks expressed as 2θ at 13.75±0.2°, 14.70±0.2°, 14.99±0.2°, 16.11±0.2°, 16.78±0.2°, 18.50±0.2°, 19.42±0.2°, 21.66±0.2° and 22.63±0.2°.

In some embodiments, provided herein is a crystalline Form II of Compound (I) characterized by an X-ray powder diffraction pattern comprising at least three peaks selected from the peaks expressed as 2θ at 13.8±0.10, 14.7±0.10, 15.0±0.10, 16.1±0.10, 16.8±0.10, 18.5±0.10, 19.4±0.1°, 21.7±0.10 and 22.6±0.1°.

In some embodiments, provided herein is a crystalline Form II of Compound (I) characterized by an X-ray powder diffraction pattern comprising the peaks expressed as 2θ at 13.8±0.2°, 14.7±0.2°, 15.0±0.2°, 16.1±0.2°, 16.8±0.2°, 18.5±0.2°, 19.4±0.2°, 21.7±0.2° and 22.6±0.2°.

In some embodiments, provided herein is a crystalline Form II of Compound (I) characterized by an X-ray powder diffraction pattern comprising the peaks expressed as 2θ at 13.75±0.20, 14.70±0.20, 14.99±0.20, 16.11±0.20, 16.78±0.20, 18.50±0.20, 19.42±0.2°, 21.66±0.2° and 22.63±0.2°.

In some embodiments, provided herein is a crystalline Form II of Compound (I) characterized by an X-ray powder diffraction pattern comprising the peaks expressed as 2θ at 13.8±0.10, 14.7±0.10, 15.0±0.10, 16.1±0.10, 16.8±0.10, 18.5±0.10, 19.4±0.10, 21.7±0.10 and 22.6±0.1°.

In some embodiments, provided herein is a crystalline Form II of Compound (I) characterized by an X-ray powder diffraction pattern comprising peaks expressed as 2θ at 9.6±0.2°, 13.8±0.2°, 14.7±0.2°, 15.0±0.2°, 16.1±0.2°, 16.8±0.2°, 17.8±0.2°, 18.5±0.2°, 19.0±0.2°, 19.4±0.2°, 20.4±0.2°, 21.7±0.2°, 22.6±0.2°, 23.2±0.2°, and 24.5±0.2°.

In some embodiments, provided herein is a crystalline Form II of Compound (I) characterized by an X-ray powder diffraction pattern comprising peaks expressed as 2θ at 9.61±0.2°, 13.75±0.2°, 14.70±0.2°, 14.99±0.2°, 16.11±0.2°, 16.78±0.2°, 17.81±0.2°, 18.50±0.2°, 18.97±0.2°, 19.42±0.2°, 20.43±0.2°, 21.66±0.2°, 22.63±0.2°, 23.19±0.2°, 24.47±0.2°.

Figure 4:
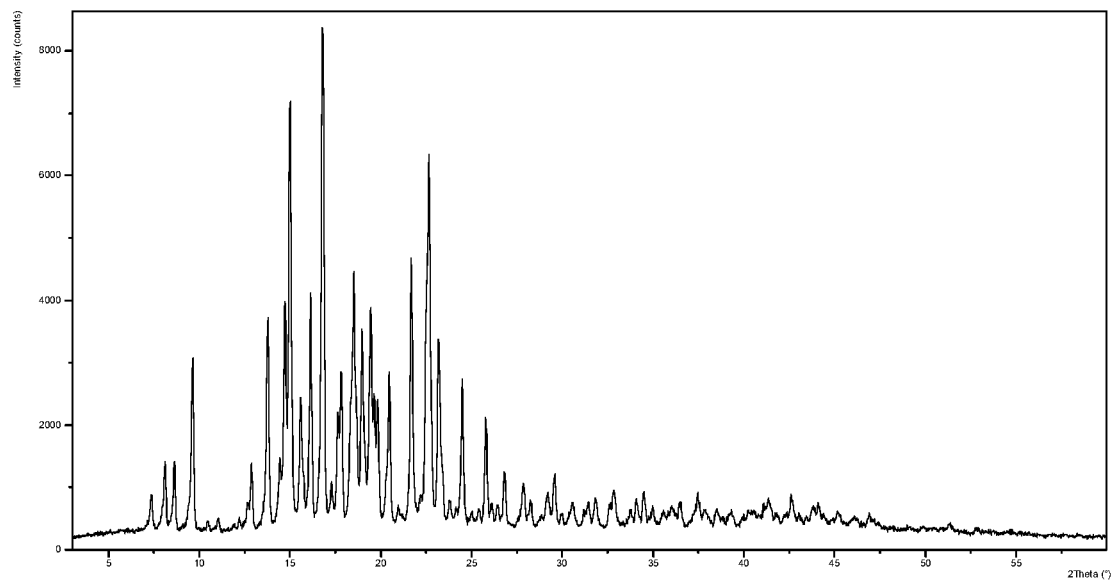
FIG. 4 shows an X-ray powder diffraction (XRPD) pattern of crystalline Form II of Compound (I).

In some embodiments, provided herein is a crystalline Form II of Compound (I) having an X-ray powder diffraction (XRPD) pattern substantially as shown in FIG. 4.

In some embodiments, provided herein is a crystalline form II of Compound (I) characterized by a differential scanning calorimetry thermogram comprising an endothermic peak at 80.53° C.±2° C.

In some embodiments, provided herein is a crystalline form II of Compound (I) characterized by a differential scanning calorimetry (DSC) having a melting endothermic peak at 75° C.-85° C., a temperature with maximum endotherm of 80.53° C., and the melting enthalpy is 70.31 J/g, when measured using a heating rate of 10° C./min.

Figure 5:
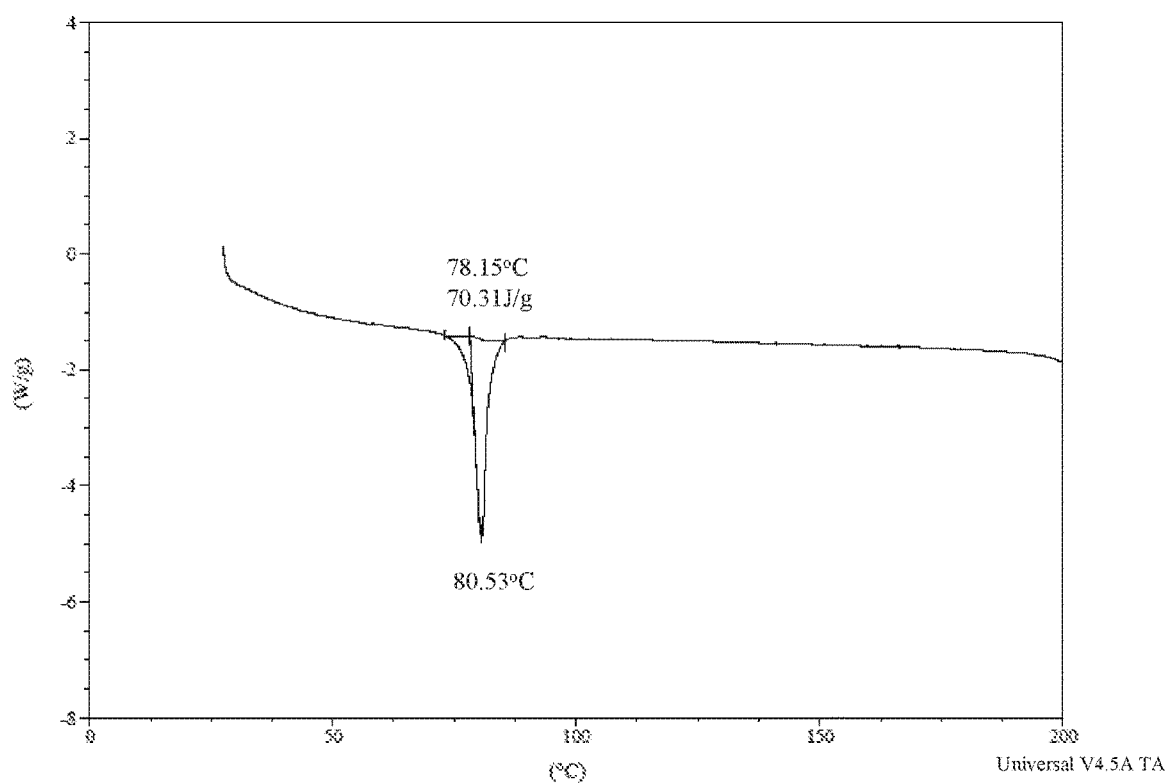
FIG. 5 shows a differential scanning calorimetry (DSC) thermogram of crystalline Form II of Compound (I).

In some embodiments, provided herein is a crystalline Form II of Compound (I) having a differential scanning calorimetry thermogram substantially as shown in FIG. 5.

In some embodiments, provided herein is a crystalline Form II of Compound (I) having a thermogravimetric analysis (TGA) with no significant weight loss at 150° C. before the degradation process begins. The detected weight loss from 25° C. to 150° C. is less than 2.15 wt % and is equivalent to dry loss, which may be attributable to the small amount of water or solvents adsorbed by the sample.

Figure 6:
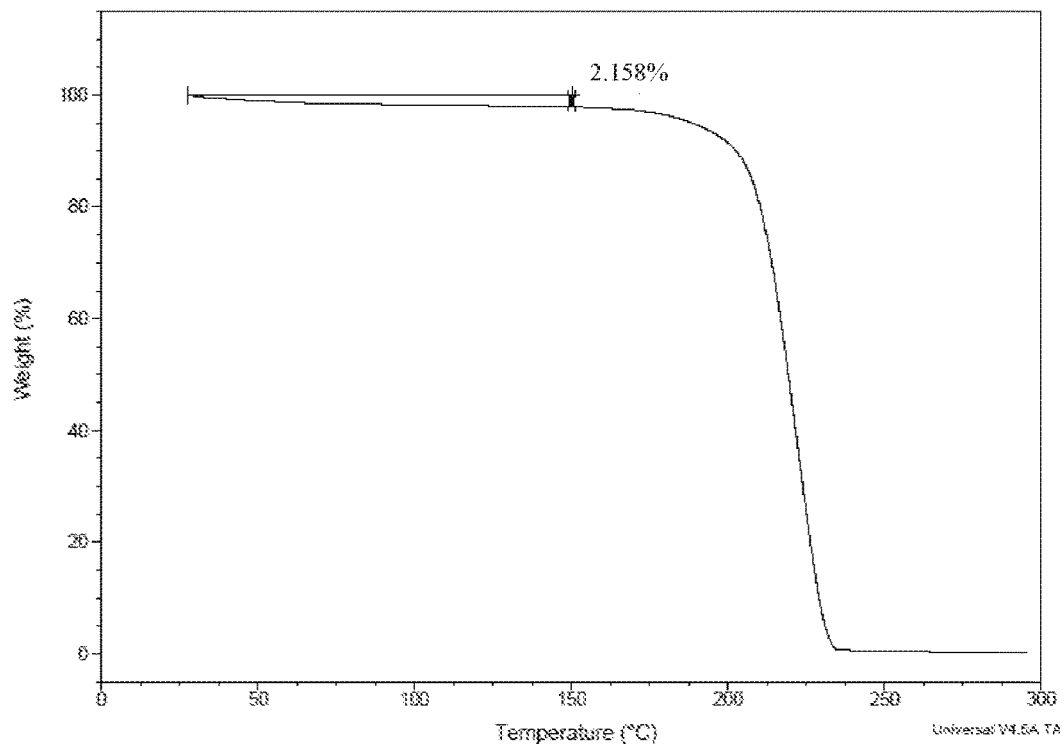
FIG. 6 shows a thermogravimetric analysis (TGA) curve of crystalline Form II of Compound (I).

In some embodiments, provided herein is a crystalline Form II of Compound (I) having a thermogravimetric analysis curve substantially as shown in FIG. 6.

Two or more features of crystalline Form II of Compound (I) may be combined.

Pharmaceutical Composition

In another aspect, provided is pharmaceutical composition comprising a crystalline form, such as crystalline Form I or II, of Compound (I) or a combination thereof, and a pharmaceutically acceptable excipient.

In some embodiments, provided is a pharmaceutical composition comprising Compound (I), wherein at least 80% of Compound (I) is in a crystalline form as described herein. In some embodiments, the pharmaceutical composition comprises Compound (I), wherein at least 80% of Compound (I) is in Form I. In some embodiments, the pharmaceutical composition comprises Compound (I), wherein at least 80% of Compound (I) is in Form II.

In some embodiments, provided is a pharmaceutical composition comprising Compound (I), wherein at least 90% of Compound (I) is in a crystalline form as described herein. In some embodiments, the pharmaceutical composition comprises Compound (I), wherein at least 90% of Compound (I) is in Form I. In some embodiments, the pharmaceutical composition comprises Compound (I), wherein at least 90% of Compound (I) is in Form II.

In some embodiments, provided is a pharmaceutical composition comprising Compound (I), wherein at least 95% of Compound (I) is in a crystalline form as described herein. In some embodiments, the pharmaceutical composition comprises Compound (I), wherein at least 95% of Compound (I) is in Form I. In some embodiments, the pharmaceutical composition comprises Compound (I), wherein at least 95% of Compound (I) is in Form II.

Selection of a pharmaceutically acceptable excipient depends on the use and expected administration method. For the pharmaceutical composition comprising a crystalline form of Compound (I), the excipient preferably maintains the active compound whether in a crystalline form or not. In other words, Compound (I) should not substantially change when combined with the excipient. The excipient should not be incompatible with Compound (I), for example, by producing any unwanted biological action or interacting with any other component of the pharmaceutical composition in a harmful manner.

The pharmaceutical composition may be prepared by known methods in the Pharmaceutical preparation field, for example, see Remington's Pharmaceutical Sciences, 18th edition, (Mack Publishing Company, Easton, Pa., 1990).

Suitable pharmaceutically acceptable excipients may include, for example, inert solid diluents and fillers, diluents, including sterile aqueous solution and various organic solvents, permeation enhancers, solubilizers and other excipients. Such compositions are prepared in a manner well known in the pharmaceutical art. See, e.g., Remington's Pharmaceutical Sciences; and Modern Pharmaceutics, Marcel Dekker, Inc. 3rd Ed. (G. S. Banker & C. T. Rhodes, Eds.). The pharmaceutical compositions may be administered alone or in combination with other therapeutic agents.

Exemplary excipients include sodium citrate or dicalcium phosphate, or (a) fillers such as starch, lactose, sucrose, glucose, mannose and silicic acid; (b) binders such as cellulose derivatives, starch, alginate, gelatin, polyethylene pyrrolidone, sucrose and gum arabic; (c) moisturizing agents such as glycerol; (d) disintegrating agents such as agar, calcium carbonate, potato starch or cassava starch, alginate, cross-linked carboxymethyl cellulose sodium, complexing silicate and sodium carbonate; (e) solution blockers, such as paraffin wax; (f) absorption accelerators, such as quaternary ammonium compounds; (g) wetting agents such as whale wax and glycerin monostearate, magnesium stearate, etc.; (h) adsorbents such as kaolin and bentonite; and (i) lubricants such as talc, calcium stearate, magnesium stearate, solid polyethylene glycol, sodium 12 alkyl sulfate or their mixtures. In the case of capsules, tablets and pills, the dosage form may also contain a buffer.

Other excipients include but are not limited to preservatives, aerosols, sweeteners, flavorings, fragrances, emulsifiers and dispersants. A variety of antibacterial agents and antifungal agents, such as P-hydroxybenzoate, chloro-butanol, phenol, sorbic acid, etc., can facilitate the inhibition of microbial action. Excipients can also include isotonic agents such as sugar, sodium chloride and so on. If necessary, the pharmaceutical composition may also comprise a small amount of ancillary substances, such as wetting agents or emulsifiers, pH buffers, and antioxidants (e.g. citric acid, dehydrated sugar glycol mono-lauric acid ester, triethanolamine oleic acid ester and butyl hydroxy toluene).

The pharmaceutical compositions may comprise from about 0.01% to about 90%, 0.01% to about 75%, or about 0.01% to about 50%, or about 0.01% to about 25%, or about 0.01% to about 10%, or about 0.01% to about 1% w/w of one or more emulsifying agents, wetting agents or suspending agents. Such agents include, but are not limited to, polyoxyethylene sorbitan fatty esters or polysorbates, including, but not limited to, polyethylene sorbitan monooleate (Polysorbate 80), polysorbate 20 (polyoxyethylene (20) sorbitan monolaurate), polysorbate 65 (polyoxyethylene (20) sorbitan tristearate), polyoxyethylene (20) sorbitan mono-oleate, polyoxyethylene (20) sorbitan monopalmitate, polyoxyethylene (20) sorbitan monostearate; lecithins; alginic acid; sodium alginate; potassium alginate; ammonium alginate; calcium alginate; propane-1,2-diol alginate; agar; carrageenan; locust bean gum; guar gum; tragacanth; acacia; xanthan gum; karaya gum; pectin; amidated pectin; ammonium phosphatides; microcrystalline cellulose; methyl cellulose; hydroxypropylcellulose; hydroxypropylmethylcellulose; ethylmethylcellulose; carboxymethylcellulose; sodium, potassium and calcium salts of fatty acids; mono- and di-glycerides of fatty acids; acetic acid esters of mono- and di-glycerides of fatty acids; lactic acid esters of mono- and di-glycerides of fatty acids; citric acid esters of mono- and di-glycerides of fatty acids; tartaric acid esters of mono- and di-glycerides of fatty acids; mono- and diacetyl-tartaric acid esters of mono- and di-glycerides of fatty acids; mixed acetic and tartaric acid esters of mono- and di-glycerides of fatty acids; sucrose esters of fatty acids; sucroglycerides; polyglycerol esters of fatty acids; polyglycerol esters of poly-condensed fatty acids of castor oil; propane-1,2-diol esters of fatty acids; sodium stearoyl-2-lactylate; calcium stearoyl-2-lactylate; stearoyl tartrate; sorbitan monostearate; sorbitan tristearate; sorbitan monolaurate; sorbitan monooleate; sorbitan monopalmitate; extract of *quillaia*; polyglycerol esters of dimerised fatty acids of soya bean oil; oxidatively polymerised soya bean oil; and pectin extract. In certain embodiments herein, the present formulations comprise polysorbate 80, microcrystalline cellulose, carboxymethylcellulose sodium and/or dextrose.

The pharmaceutical compositions may comprise from about 0.01% to about 90%, or about 0.01% to about 75%, or about 0.01% to about 50%, or about 0.01% to about 25%, or about 0.01% to about 10%, or about 0.01% to about 1% of one or more excipients and additives which are pharmacologically suitable. Excipients and additives generally have no pharmacological activity, or at least no undesirable pharmacological activity. The concentration of these may vary with the selected agent, although the presence or absence of these agents, or their concentration is not an essential feature of the invention. The excipients and additives may include, but are not limited to, surfactants, moisturizers, stabilizers, complexing agents, antioxidants, or other additives known in the art. Complexing agents include, but are not limited to, ethylenediaminetetraacetic acid (EDTA) or a salt thereof, such as the disodium salt, citric acid, nitrilotriacetic acid and the salts thereof.

The pharmaceutical compositions also may comprise from about 0.01% to about 90%, or about 0.01% to about 75%, or about 0.01% to about 50%, or about 0.01% to about 25%, or about 0.01% to about 10%, or about 0.01% to about 10% of one or more solvents or co-solvents. Solvents or co-solvents for use herein include, but are not limited to, hydroxylated solvents or other pharmaceutically-acceptable polar solvents, such as alcohols including isopropyl alcohol, glycols such as propylene glycol, polyethylene glycol, polypropylene glycol, glycol ether, glycerol, and polyoxyethylene alcohols. In another embodiment, the pharmaceutical compositions may comprise one or more conventional diluents known in the art. An example of a diluent is water.

A solid dosage form can be prepared with a coating or shell, such as enteric-coating or others known in the field. A solid dosage form can comprise a photoprotective agent or polymeric substances and waxes for delayed release of Compound (I) in some parts of the gastral intestinal tract. If appropriate, Compound (I) may be in a microencapsulated form with one or more excipients.

Pharmaceutical compositions useful for rectal administration, for example, suppositories, can be prepared by mixing a crystalline form, such as crystalline Form I or II, of Compound (I) with an irritant-free excipient (such as cocoa oil, polyethylene glycol or suppository wax), which are solids at room temperatures, but are liquid at body temperatures so that the pharmaceutical compositions melt and release Compound (I) in the appropriate body cavity.

In some embodiments, the pharmaceutical compositions are formulated as microcrystalline or nanocrystalline suspensions. In one embodiment, the solvent of the suspension is water, saline, PBS buffer, Tween-20, Span-20 or the combination thereof. In some embodiments, the suspension is prepared by a method comprising dissolving or admixing a crystalline form, such as crystalline Form I or II, of Compound (I) with a solvent, such as demonstrated in the Examples.

In some embodiments, the pharmaceutical composition comprises a pharmaceutically acceptable excipient and a crystalline form, such as crystalline Form I or II, of Compound (I), wherein the pharmaceutical composition is in a solid form or a suspension in a liquid excipient and the crystalline form may provide improved stability, handling, flowability, and/or purity, which may provide improved pharmacokinetic profile, efficacy and/or safety profile.

In some embodiments, the crystalline form such as crystalline Form I or II of Compound (I) is substantially preserved during preparation of the pharmaceutical composition, such as a solid dosage form used for oral administration, including capsules, tablets, pills, powders and granules, or a liquid suspension. In such solid formulations, the crystalline form, such as crystalline Form I or II, of Compound (I) is mixed with at least one inert, pharmaceutical acceptable excipient (also known as a pharmaceutical acceptable carrier).

In some embodiments, the pharmaceutical composition is prepared from a crystalline form, such as crystalline Form I or II, of Compound (I), which may provide improved stability, handling, purity and solubility, which may provide improved pharmacokinetic profile, efficacy and/or safety profile. In some embodiments, the pharmaceutical composition is in a liquid solution form.

In some embodiments, the pharmaceutical composition further comprises another therapeutic agent.

In some embodiments, the pharmaceutical composition further comprises a cholinesterase inhibitor.

In some embodiments, the cholinesterase inhibitor is tacrine, donepezil, huperzine-A, galanthamine, rivastigmine, or a combination thereof.

The crystalline form, such as crystalline Form I or II, of Compound (I) may be administered in a pure form or in a suitable pharmaceutical composition by any acceptable drug delivery method, such as oral, nasal, gastrointestinal (intravenous, intramuscular or subcutaneous), topical, transdermal, in the vagina, inside the bladder, in the brain pool or rectum. The pharmaceutical composition may be in a solid, semisolid, lyophilized or liquid dosage form (for example, tablet, suppository, pill, soft elasticity and gelatin capsule, powder, solution, suspension agent or aerosol agent, etc.). The pharmaceutical composition may be in a unit dosage form that is suitable for simple and accurate dosing. The amount that is administered can be determined according to the degree of severity of the disease to be treated.

The crystalline forms, such as crystalline Form I or Form II of Compound (I) may be administered to a subject orally. Oral administration may be via, for example, capsules, tablets or enteric coated tablets. In making pharmaceutical compositions comprising one or more of the forms of Compound (I) as described herein, a crystalline form, such as crystalline Form I or Form II of Compound (I) may be diluted by an excipient or enclosed within such a carrier that can be in the form of a capsule, sachet, paper or other container. When the excipient serves as a diluent, it can be in the form of a solid, semi-solid, or liquid material, which acts as a vehicle, carrier or medium for the active ingredient. Thus, the compositions can be in the form of a capsule, a tablet or pill, or the like.

In one aspect, provided is a method for preparing a pharmaceutical composition comprising Compound (I), which method comprises mixing a crystalline form, such as crystalline Form I or II, of Compound (I) with at least one pharmaceutical acceptable excipient.

Methods of Treatment

In another aspect, provided is a method of preventing, treating or lessening a central nervous system disease in a subject in need thereof comprising administering to the subject a therapeutically effective amount of a crystalline form, such as crystalline Form I or II, of Compound (I) or a pharmaceutical composition thereof.

In another aspect, provided is use of a crystalline form, such as crystalline Form I or II, of Compound (I) or a pharmaceutical composition thereof in the manufacture of a medicament for preventing, treating or lessening a central nervous system disease. In another embodiment, provided is a crystalline form, such as crystalline Form I or II, of Compound (I) or a pharmaceutical composition thereof for preventing, treating or lessening a central nervous system disease.

In some embodiments, the central nervous system disease is Parkinson syndrome, Alzheimer's disease, Huntington's disease, atrophic myelitis, AIDS dementia, vascular dementia, seizures, neuralgia, or abstinence symptoms.

In another aspect, provided is a method of preventing, treating or ameliorating the symptoms of a neurodegenerative disease in a subject in need thereof comprising administering to the subject a therapeutically effective amount of a crystalline form, such as crystalline Form I or II, of Compound (I) or a pharmaceutical composition thereof.

In another aspect, provided is use of a crystalline form, such as crystalline Form I or II, of Compound (I) or a pharmaceutical composition thereof in the manufacturing of a medicament for preventing, treating or ameliorating the symptoms of a neurodegenerative disease. In another embodiment, provided is a crystalline form, such as crystalline Form I or II, of Compound (I) or a pharmaceutical composition thereof for preventing, treating or ameliorating the symptoms of a neurodegenerative disease.

In some embodiments, the neurodegenerative disease is mediated by a N-methyl-D-aspartate (NMDA) receptor. In some embodiments, the neurodegenerative disease is selected from the group consisting of Parkinson's disease, Alzheimer's disease, Huntington's disease, atrophic myelitis, AIDS dementia, vascular dementia or combinations thereof. In some embodiments, the subject suffers from moderate to severe dementia of the Alzheimer's disease.

In another aspects, provided a method for preventing, treating or ameliorating a symptom of diabetes in a subject in need thereof, wherein the method comprises administering to the subject a crystalline form, such as crystalline Form I or II, of Compound (I) or a pharmaceutical composition thereof. In some embodiments, the diabetes comprises type I or type II diabetes.

In some embodiments, provided is use of a crystalline form, such as crystalline Form I or II, of Compound (I) or a pharmaceutical composition thereof for the manufacturing of a medicament for preventing, treating or ameliorating the symptoms of diabetes. In some embodiments, provided is a crystalline form, such as crystalline Form I or II, of Compound (I) or a pharmaceutical composition thereof for preventing, treating or ameliorating the symptoms of diabetes. In some embodiments, the diabetes comprises type I or type II diabetes.

Methods of administering pharmaceutical compositions are well known to those of ordinary skill in the art and include, but are not limited to, oral, microinjection, intravenous or parenteral administration. The compositions may be intended for topical, oral, or local administration as well as intravenously, subcutaneously, or intramuscularly. Administration can be effected continuously or intermittently throughout the course of the treatment. Methods of determining the most effective means and dosage of administration are well known to those of skill in the art and will vary with the disease being treated and the subject being treated. Single or multiple administrations can be carried out with the dose level and pattern being selected by the treating physician. In some embodiments, the therapeutically effective amount of a crystalline form, such as crystalline Form I or II, of Compound (I) or a pharmaceutical composition thereof is an amount when administered that provide a therapeutically effective amount of memantine in vivo.

Combination Therapy

The crystalline forms of Compound (I), such as Form I or Form II, may be combined with one or more additional therapeutic agents.

In some embodiments, the crystalline forms of Compound (I), such as Form I or Form II, may be administered sequentially with the additional therapeutic agent(s). When administered sequentially, the form of Compound (I) as described herein and the additional therapeutic agent(s) may be administered in two or more administrations, and contained in separate compositions or dosage forms, which may be contained in the same or different package or packages.

In some embodiments, the crystalline forms of Compound (I), such as Form I or Form II, may be administered simultaneously with the additional therapeutic agent(s).

When administered simultaneously, the form of Compound (I) as described herein and the additional therapeutic agent(s) may be in separate compositions or dosage forms, or the same composition or dosage form.

In some embodiments, the crystalline forms of Compound (I), such as Form I or Form II, may be combined with one or more additional therapeutic agents in a unitary dosage form (for example for oral administration). In some embodiments, a crystalline form of Compound (I) as described herein and the one or more additional agents may be in separate dosage forms.

In some embodiments, the additional therapeutic agent is useful in preventing, treating or lessening a central nervous system disease in a subject.

In some embodiments, the additional therapeutic agent comprises a cholinesterase inhibitor. In some embodiments, the cholinesterase inhibitor is tacrine, donepezil, huperzine-A, galanthamine, rivastigmine, or a combination thereof.

Preparation

Crystalline forms of Compound (I) may be prepared in a variety of ways, including but not limited to, for example, crystallization or recrystallization from a suitable solvent mixture, sublimation, conversion from another phase of solid state, crystallization from supercritical fluids, and spray. The crystallization or recrystallization of a crystalline form from a solvent mixture includes but is not limited to, for example, solvent evaporation; decrease of the temperature of the solvent mixture, the crystal seeding of a supersaturated solvent mixture of Compound (I), freeze-drying a solvent mixture, and addition of an antisolvent to a solvent mixture. Crystalline forms can be prepared by high yield crystallization technique, including polymorph.

The characterization of crystalline forms is discussed in Solid-State Chemistry of Drugs, S. R. Byrn, R. R. Pfeiffer- and J. G. Stowell, second edition, SSCI, West Lafayette, Ind. (1999).

In one aspect, provided is a method of preparing a crystalline form of Compound (I), such as Form I or Form II.

In some embodiments, provided is a method of preparing crystalline Form I of Compound (I) comprising cooling a solution of Compound (I) in a solvent, such as acetonitrile or isopropanol. In some embodiments, the temperature of the solution is cooled to room temperature. In some embodiments, the temperature of the solution is cooled to below 0° C. In some embodiments, the temperature of the solution prior to cooling is sufficient to dissolve Compound (I), such as about 40° C. In some embodiments, provided is a method of preparing crystalline Form I of Compound (I) comprising adding an antisolvent, such as water, to a solution of Compound (I) in a solvent, such as isopropanol, acetonitrile or acetone.

In some embodiments, provided is a method of preparing crystalline Form II of Compound (I) comprising adding an antisolvent, such as water, to a solution of Compound (I) in a solvent, such as dimethylsulfoxide, glycol dimethyl ether or ethanol.

A cooled crystalline mixture can be filtered in a vacuum, and the separated solid product can be washed with a suitable solvent (e.g., a cold recrystallization solvent). After washing, the product can be dried in nitrogen to obtain the desired crystalline form. The product may be analyzed by suitable spectral or analytical techniques, including, but not limited to, differential scanning calorimetry (DSC), X-ray powder diffraction (XRPD) and thermogravimetric analysis (TGA) to assess whether a crystalline form of the compound has been formed. The resulting crystalline form can be generated in a separation yield of more than about 70% of the weight of the compound initially used in the crystallization process, preferably greater than about 90%. The product may be further grinded or sieve through a screen.

EXAMPLES

Upon reading the detailed description, a person skilled in the relevant art will understand the characteristics and advantages of the crystalline forms. It is to be understood that, for brevity reasons, the different features of this disclosure that are described in the context of a single embodiment can also be combined to form their subgroups, and may be modified, adjusted, substituted or varied. The following examples illustrate certain embodiments and shall not be construed as limiting the scope or spirit of the disclosure to the specific steps described therein.

Example 1. Preparation of ((((1r,3R,5S,7r)-3,5-dimethyladamantan-1-yl)carbamoyl)oxy)methyl Benzoate (Compound (I))

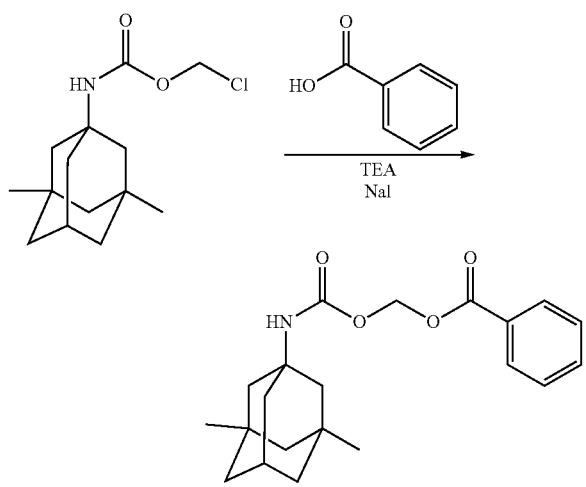

To a 100 mL single neck flask were added chloromethyl ((1r,3R,5S,7r)-3,5-dimethyladamantan-1-yl)carbamate (2.0 g, 7.35 mmol), benzoic acid (0.98 g, 8.09 mmol), triethylamine (0.89 g, 8.82 mmol), sodium iodide (0.55 g, 3.67 mmol) and N,N-dimethyl formamide (8 mL). The mixture was heated to 85° C. After 2 hours of reaction, a sample was taken and analyzed by TLC. After the reaction completed, the mixture was cooled to room temperature, and then water (30 mL) and ethyl acetate (30 mL) were added. The mixture was stirred at room temperature for 30 min, and then allowed to partitioned. The organic layer was separated and washed with saturated aqueous sodium bicarbonate solution (30 mL) once, then HCl (0.5 M, 30 mL) once, and lastly water (30 mL) once. The organic layer was separated and concentrated in vacuo to remove ethyl acetate to give a brown oil (1.2 g). The brown oil was purified by column chromatography to obtain a white solid (0.7 g, 26.6%).

$^1$H NMR spectra were recorded using Bruker 400 MHz or 600 MHz NMR spectroscopy. The solid state $^{13}$C NMR spectroscopy uses bruker 100 MHz nuclei at ambient temperature (from 21-25° C.). $^1$H NMR spectra are CDCl$_3$, DMSO-D$_6$, CD$_3$OD or acetone as solvents (in ppm), with TMS (0 ppm) or chloroform (7.25 ppm) as the reference standard. When multiple peaks occur, the following abbreviations are used: s (singlet), d (doublet), t (triplet), m (multiplet), br (broadened), dd (doublet of doublets), dt (doublet of triplets). Coupling constant (J) is expressed in hertz (Hz).

Low-resolution mass spectrometry (MS) data is measured in terms of: Agilent 6120 four-pole HPLC-M (Post type: Zorbax sb-c18, 2.1×mm, 3.5 microns, 6 min, flow rate 0.6 mL/min. Mobile phase: 5%-95% (0.1% carboxylic acid in $CH_3CN$) in $H_2O$ (including 0.1% carboxylic acid), using electrospray ionization (ESI), under 210 nm/254 nm UV detection.

LC/MS (ESI, pos, ion) m/z: 381 [M+Na]$^+$; LC/MS (ESI, pos, ion) m/z: 737 [2M+Na]$^+$; $^1$H NMR (600 MHz, DMSO-$d_6$) δ (ppm): 8.02-7.92 (m, 2H), 7.70 (t, J=7.4 Hz, 1H), 7.56 (t, J=7.8 Hz, 2H), 7.33 (s, 1H), 5.85 (s, 2H), 2.06 (d, J=2.5 Hz, 1H), 1.69 (s, 2H), 1.51 (q, J=11.8 Hz, 4H), 1.26 (dd, J=32.6, 11.8 Hz, 4H), 1.08 (s, 2H), 0.80 (s, 6H).

Example 2. In Vivo Pharmacokinetics Analysis of ((((1r,3R,5S,7r)-3,5-dimethyladamantan-1-yl)carbamoyl)oxy)methyl Benzoate (Compound (I))

Compound (I) was tested in an experiment to determine its in vivo conversion to the active compound memantine.
Materials and Methods Analytical LC/MS/MS systems: Agilent 1200 Series vacuum degasser, dual-injection pump, orifice autosampler, column incubator, charged spray ionization (ESI) source, and Agilent G6430 three-stage quadrupole mass spectrometer. The quantitative analysis is performed in the MRM mode, with the following MRM conversion parameters:

| | |
|---|---|
| Multi-reaction detection scan | 180.2→163.1 |
| Fragmentation voltage | 15 V |
| Capillary voltage | 3500 V |
| Dryer temperature | 350° C. |
| Atomizer | 40 psi |
| Dryer flow rate | 9 L/min |

Waters XBridge TMC18, 2.1×30 mm, 3.5 µM column; 20 µL of sample was injected in each run. Conditions: The mobile phase included ammonium formate+2 mM ammonium formate+0.1% formic acid (A) and methanol+2 mM ammonium formate+0.1% formic acid (B). The flow rate was 0.35 mL/min. The mobile phase gradient is as follows:

| Time | Mobile Phase B Gradient |
|---|---|
| 0.8 min | 10% |
| 1.4 min | 75% |
| 2.6 min | 95% |
| 2.7 min | 10% |
| 3.5 min | stop |

Additional instruments and reagents included Agilent 6330 Series LC/MS/MS spectrometer equipped with a G1312A Binary Injection Pump, G1367A autosampler and MS/MS Detector for analysis; LC/MS/MS spectrometer with ESI source. Suitable cationic model treatments and MRM conversion were used for each analyte using standard solution for optimal analysis. Waters XBridge TMC18 was used with specifications of 2.1×30 mm, 3.5 µM. The reaction was carried out with ammonium formate+2 mM ammonium formate+0.1% formic acid (A) and methanol+2 mM ammonium formate+0.1% formic acid (B). The flow rate was 0.35 mL/min; the column temperature was maintained at 40° C.; 10 µL of sample was injected.

Memantine and Compound (I) were subjected to pretreatment including grinding and sieving, and were dissolved or dispersed in Tween-20 and/or Span-20 to form a solution or suspension. The suspension was pulverized by a ball mill before administration. Memantine (17.5 mg/kg) or Compound (I) (75 or 37.5 mg/kg) was administered to rats by intramuscular administration. Whole blood was collected at 0.25, 1, 2, 5, 7, 24, 48, 72, 96, 120, 148 and 196 hours, and centrifuged at 12,000 G for 2 minutes. Plasma was collected and stored at −20° C. or −70° C. until the LC/MS/MS analysis was performed.

Table 1 provides the pharmacokinetics (PK) data in terms of the AUC, $C_{max}$, $T_{1/2}$ and $T_{max}$ of memantine measured in rats when memantine or Compound (I) was administered. Compound (I) exhibited excellent pharmacokinetic properties and sustained release of meantine with respect to peak time ($T_{max}$), half-life ($T_{1/2}$) and exposure ($AUC_{last}$). The absorption and release curves were more flat than the control (memantine in solution). The meantine $T_{max}$ generated by Compound (I) was about 180 hours.

TABLE 1

In vivo Pharmacokinetics Properties of the Compounds

| Sample | Formulation | Dose (mg/kg) | $AUC_{last}$ (hour * ng/mL) | $C_{max}$ (ng/mL) | $T_{1/2}$ (hours) | $T_{max}$ (hours) |
|---|---|---|---|---|---|---|
| memantine | solution | 17.5 | 11767 | 1945 | 4 | 1.33 |
| Compound (I) | suspension | 75 | 4718 | 38.2 | N/A* | 180 |

*N/A: not obtained due to flat concentration curve

The data show that Compound (I) possesses favorable slower release of the active compound memantine in vivo, and thereby is useful in treating diseases.

Example 3. Preparation of Crystalline Form I of ((((1r,3R,5S,7r)-3,5-dimethyladamantan-1-yl)carbamoyl)oxy)methyl Benzoate To anhydrous isopropanol (20 mL) was added ((((1r,3R,5S,7r)-3,5-dimethyladamantan-1-yl)carbamoyl)oxy)methyl benzoate (2.00 g) crude product. The mixture was stirred at 40° C. in an oil bath to get a clear solution, and then the solution was cooled to room temperature slowly, followed by slow and dropwise addition of water (20 mL). After a white solid precipitated, the mixture was filtered by suction, and the filter cake was dried in vacuo in a drying oven at room temperature to get white crystal (1.88 g, 94%), which was crystalline Form I identified by XPRD and DSC.

Example 4. Preparation of Crystalline Form I of (((((1r,3R,5S,7r)-3,5-dimethyladamantan-1-yl)carbamoyl)oxy)methyl Benzoate To acetone (1 mL) was added ((((1r,3R,5S,7r)-3,5-dimethyladamantan-1-yl) carbamoyl)oxy)methyl benzoate (80 mg) to get a clear solution, followed by slow and dropwise addition of water (1 mL). After a white solid precipitated, the mixture was filtered by suction, and the filter cake was dried in vacuo in a drying oven at room temperature to get white crystal (60 mg, 75%), which was crystalline Form I identified by XPRD and DSC.

Example 5. Preparation of Crystalline Form I of (((((1r,3R,5S,7r)-3,5-dimethyladamantan-1-yl)carbamoyl)oxy)methyl Benzoate To acetonitrile (1 mL) was added ((((1r,3R,5S,7r)-3,5-dimethyladamantan-1-yl)carbamoyl)oxy)methyl benzoate (80 mg) to get a clear solution, followed by slow and dropwise addition of water (1 mL). After a white solid precipitated, the mixture was filtered by suction, and the filter cake was dried in vacuo in a drying oven at room temperature to get white crystal (65 mg, 81.25%), which was crystalline Form I identified by XPRD and DSC.

Example 6. Preparation of Crystalline Form I of (((((1r,3R,5S,7r)-3,5-dimethyladamantan-1-yl)carbamoyl)oxy)methyl Benzoate To acetonitrile (0.5 mL) was added ((((1r,3R,5S,7r)-3,5-dimethyladamantan-1-yl)carbamoyl)oxy)methyl benzoate (500 mg) at 40° C. to get a clear solution, followed by slow cooling of the solution to −5° C. After a white solid precipitated, the mixture was filtered by suction, and the filter cake was dried in vacuo in a drying oven at room temperature to get white crystal (430 mg, 86%), which was crystalline Form I identified by XPRD and DSC.

Example 7. Preparation of Crystalline Form II of (((((1r,3R,5S,7r)-3,5-dimethyladamantan-1-yl)carbamoyl)oxy)methyl Benzoate To anhydrous ethanol (20 mL) was added ((((1r,3R,5S,7r)-3,5-dimethyladamantan-1-yl)carbamoyl)oxy)methyl benzoate (2.00 g) to get a clear solution, followed by slow and dropwise addition of water (15 mL). After a white solid precipitated, the mixture was continuously stirred for 2 hours and filtered by suction. The filter cake was dried in vacuo in a drying oven at room temperature to get white crystal (1.83 g, 91.5%), which was crystalline Form II identified by XPRD and DSC.

Example 8. Preparation of Crystalline Form II of (((((1r,3R,5S,7r)-3,5-dimethyladamantan-1-yl)carbamoyl)oxy)methyl Benzoate To dimethylsulfoxide (10 mL) was added ((((1r,3R,5S,7r)-3,5-dimethyladamantan-1-yl)carbamoyl)oxy)methyl benzoate (2.00 g) to get a clear solution, followed by slow and dropwise addition of water (10 mL). After a white solid precipitated, the mixture was continuously stirred for 2 hours and filtered by suction. The filter cake was dried in vacuo in a drying oven at room temperature to get white crystal (1.93 g, 96.5%), which was crystalline Form II identified by XPRD and DSC.

Example 9. Preparation of Crystalline Form II of (((((1r,3R,5S,7r)-3,5-dimethyladamantan-1-yl)carbamoyl)oxy)methyl Benzoate To glycol dimethyl ether (1 mL) was added ((((1r,3R,5S,7r)-3,5-dimethyladamantan-1-yl) carbamoyl)oxy)methyl benzoate (200 mg) at 50° C. to get a clear solution, and then water (1 mL) was added dropwise, following by cooling of the mixture to room temperature. After a white solid precipitated, the mixture was continued to stir for 2 hours and filtered by suction, and then the filter cake was dried in vacuo in a drying oven at room temperature to get white crystal (160 mg, 80%). The obtained crystal was crystalline Form II identified by XPRD and DSC.

Example 10. Characterization of Crystalline Forms of (((((1r,3R,5S,7r)-3,5-dimethyladamantan-1-yl) carbamoyl)oxy)methyl Benzoate 1. X-Ray Powder Diffraction (XPRD)

X-ray powder diffraction data were collected and recorded on Netherlands PANalytical Empyrean X-ray diffractometer equipped with transmission and reflection sample stage with an automated 3*15 zero background sample holder. The radiation source was (Cu, kα, Kα1 (Å): 1.540598; Kα2 (Å): 1.544426; Kα2/Kα1 intensity ratio: 0.50), wherein voltage was 45 KV, current was 40 mA. X-Ray angular spread, i.e. effective sample size constrained by X-ray was 10 mm. An effective 2θ range of 3° to 600 was obtained by using a mode of θ-θ continuously scanning. An appropriate amount of a sample was pressed gently using a clean glass slide in circular groove of the zero background sample holder under ambient conditions (about 18° C. to 32° C.) to get a flat surface. The zero background sample holder was fixed. The sample was analyzed in the range of from 3° to 60° 2θ±0.2° with a 0.0167° step size to produce a traditional XRPD figure. Data were collected by Data Collector software, analyzed by HighScore Plus software, and displayed by Data Viewer.

FIG. 1 shows an XPRD pattern of crystalline Form I of Compound (I) obtained at room temperature (about 25° C.). A list of peaks is shown in Table 2 (peak positions are shown by numbers outside of parentheses).

TABLE 2

X-ray powder diffraction data of crystalline Form I

| Position [°2θ] | d-Spacing [Å] | Relative intensity [%] | Position [°2θ] | d-Spacing [Å] | Relative intensity [%] |
|---|---|---|---|---|---|
| 7.0430(7) | 12.54085 | 27.05 | 25.890(5) | 3.43863 | 3.22 |
| 7.6813(6) | 11.50010 | 36.79 | 26.4788(6) | 3.36346 | 35.88 |
| 8.8842(5) | 9.94559 | 44.55 | 26.980(1) | 3.30212 | 25.60 |
| 9.306(2) | 9.49585 | 5.73 | 27.306(3) | 3.26341 | 6.36 |
| 10.6891(7) | 8.26995 | 23.41 | 27.606(3) | 3.22866 | 4.37 |
| 11.841(5) | 7.46763 | 1.77 | 28.699(2) | 3.10809 | 6.79 |
| 13.122(1) | 6.74133 | 13.61 | 29.393(3) | 3.03631 | 4.35 |
| 13.306(2) | 6.64875 | 5.07 | 29.886(1) | 2.98732 | 19.99 |
| 14.1751(6) | 6.24301 | 50.17 | 30.299(2) | 2.94753 | 17.64 |
| 14.644(2) | 6.04397 | 5.87 | 30.482(6) | 2.93025 | 12.53 |
| 15.069(3) | 5.87478 | 29.79 | 31.769(3) | 2.81439 | 5.03 |
| 15.185(4) | 5.82983 | 7.20 | 32.601(2) | 2.74444 | 8.46 |

TABLE 2-continued

X-ray powder diffraction data of crystalline Form I

| Position [°2θ] | d-Spacing [Å] | Relative intensity [%] | Position [°2θ] | d-Spacing [Å] | Relative intensity [%] |
|---|---|---|---|---|---|
| 15.4378(3) | 5.73511 | 100.00 | 33.467(4) | 2.67543 | 3.20 |
| 16.7349(7) | 5.29339 | 45.52 | 34.307(4) | 2.61175 | 3.82 |
| 16.911(2) | 5.23878 | 13.09 | 34.787(5) | 2.57684 | 2.08 |
| 17.6574(6) | 5.01887 | 43.23 | 35.601(9) | 2.51973 | 2.32 |
| 17.9634(4) | 4.93406 | 78.08 | 35.985(8) | 2.49372 | 2.41 |
| 18.7413(7) | 4.73097 | 49.36 | 37.181(4) | 2.41624 | 4.04 |
| 18.988(1) | 4.67011 | 22.55 | 38.63(1) | 2.32876 | 2.45 |
| 19.1660(7) | 4.62709 | 44.00 | 39.044(2) | 2.30510 | 10.15 |
| 19.645(3) | 4.51527 | 4.47 | 39.44(1) | 2.28292 | 1.76 |
| 19.925(2) | 4.45254 | 7.11 | 39.87(3) | 2.25917 | 1.23 |
| 20.555(3) | 4.31747 | 5.05 | 40.868(2) | 2.20638 | 6.86 |
| 20.994(4) | 4.22806 | 3.84 | 41.919(3) | 2.15341 | 5.38 |
| 21.399(2) | 4.14897 | 56.20 | 42.080(4) | 2.14556 | 3.31 |
| 21.552(1) | 4.11998 | 59.90 | 43.560(3) | 2.07601 | 6.81 |
| 22.138(3) | 4.01222 | 13.18 | 45.22(1) | 2.00354 | 1.91 |
| 22.3603(7) | 3.97277 | 50.16 | 45.691(7) | 1.98402 | 2.52 |
| 22.603(2) | 3.93060 | 13.68 | 46.342(4) | 1.95767 | 3.20 |
| 22.8090(7) | 3.89563 | 48.10 | 46.68(1) | 1.94440 | 1.38 |
| 23.371(3) | 3.80320 | 5.83 | 48.26(3) | 1.88428 | 0.81 |
| 23.631(1) | 3.76202 | 15.29 | 48.966(6) | 1.85874 | 2.81 |
| 23.8596(9) | 3.72641 | 26.35 | 49.40(1) | 1.84333 | 1.46 |
| 24.100(5) | 3.68983 | 3.00 | 50.870(5) | 1.79353 | 1.75 |
| 24.725(2) | 3.59792 | 5.59 | 53.120(5) | 1.72275 | 1.64 |
| 25.284(1) | 3.51962 | 14.66 | 54.302(4) | 1.68801 | 1.80 |
| 25.505(7) | 3.48969 | 6.12 | 58.02(2) | 1.58831 | 0.63 |

FIG. 4 shows an XPRD pattern of crystalline Form II of Compound (I) obtained at room temperature (about 25° C.). A list of peaks is shown in Table 3 (peak positions are shown by numbers outside of parentheses).

TABLE 3

X-ray powder diffraction data of crystalline Form II

| Position [°2θ] | d-Spacing [Å] | Relative intensity [%] | Position [°2θ] | d-Spacing [Å] | Relative intensity [%] |
|---|---|---|---|---|---|
| 7.339(2) | 12.03640 | 6.39 | 27.54(1) | 3.23604 | 1.19 |
| 8.093(1) | 10.91595 | 13.11 | 27.829(2) | 3.20327 | 9.06 |
| 8.617(1) | 10.25365 | 12.50 | 28.230(3) | 3.15868 | 5.16 |
| 9.6158(6) | 9.19048 | 31.11 | 28.80(1) | 3.09762 | 1.73 |
| 10.468(5) | 8.44443 | 1.65 | 29.171(3) | 3.05890 | 6.40 |
| 11.034(3) | 8.01249 | 2.35 | 29.550(2) | 3.02050 | 11.63 |
| 12.199(5) | 7.24934 | 1.70 | 29.944(6) | 2.98161 | 2.39 |
| 12.669(4) | 6.98156 | 4.45 | 30.4(3) | 2.93590 | 1.16 |
| 12.866(1) | 6.87517 | 12.28 | 30.540(7) | 2.92477 | 3.98 |
| 13.7563(6) | 6.43213 | 39.71 | 31.200(8) | 2.86438 | 3.07 |
| 14.435(3) | 6.13130 | 10.22 | 31.419(5) | 2.84495 | 4.68 |
| 14.7081(7) | 6.01795 | 41.55 | 31.815(3) | 2.81045 | 5.67 |
| 14.9890(5) | 5.90580 | 78.71 | 32.578(5) | 2.74630 | 4.42 |
| 15.598(1) | 5.67657 | 20.65 | 32.821(3) | 2.72655 | 7.39 |
| 16.1185(5) | 5.49440 | 43.54 | 33.727(6) | 2.65534 | 3.09 |
| 16.7817(3) | 5.27872 | 100.00 | 34.084(3) | 2.62832 | 5.34 |
| 17.284(1) | 5.12648 | 9.92 | 34.473(2) | 2.59958 | 7.76 |
| 17.630(1) | 5.02657 | 23.50 | 34.946(4) | 2.56545 | 3.54 |
| 17.8097(8) | 4.97629 | 33.34 | 35.54(1) | 2.52412 | 2.53 |
| 18.3215(7) | 4.83842 | 25.64 | 36.019(9) | 2.49150 | 3.52 |
| 18.502(1) | 4.79171 | 45.10 | 36.463(4) | 2.46215 | 5.20 |
| 18.9769(8) | 4.67275 | 33.34 | 37.422(5) | 2.40123 | 5.58 |
| 19.421(2) | 4.56690 | 39.72 | 37.879(8) | 2.37329 | 2.57 |
| 19.628(2) | 4.51930 | 21.54 | 38.494(5) | 2.33677 | 3.57 |
| 19.809(2) | 4.47824 | 23.34 | 38.819(7) | 2.31796 | 2.11 |
| 20.4314(8) | 4.34328 | 28.03 | 39.237(7) | 2.29424 | 2.67 |
| 20.99(1) | 4.22889 | 1.81 | 40.38(2) | 2.23171 | 2.75 |
| 21.6673(5) | 4.09824 | 60.74 | 41.091(3) | 2.19491 | 4.13 |
| 22.25(4) | 3.99180 | 2.87 | 41.354(8) | 2.18152 | 5.24 |
| 22.463(2) | 3.95482 | 30.57 | 41.795(7) | 2.15951 | 2.31 |
| 22.634(1) | 3.92532 | 69.30 | 42.597(4) | 2.12073 | 5.25 |
| 23.1949(8) | 3.83167 | 37.46 | 43.066(3) | 2.09871 | 3.32 |
| 23.795(3) | 3.73641 | 4.68 | 43.462(4) | 2.08049 | 3.34 |

TABLE 3-continued

X-ray powder diffraction data of crystalline Form II

| Position [°2θ] | d-Spacing [Å] | Relative intensity [%] | Position [°2θ] | d-Spacing [Å] | Relative intensity [%] |
|---|---|---|---|---|---|
| 24.110(7) | 3.68835 | 2.48 | 43.764(5) | 2.06685 | 4.03 |
| 24.39(7) | 3.64619 | 3.46 | 44.088(2) | 2.05237 | 3.58 |
| 24.475(1) | 3.63414 | 28.04 | 44.10(3) | 2.05177 | 2.58 |
| 24.991(6) | 3.56016 | 2.50 | 45.15(1) | 2.00656 | 2.52 |
| 25.373(5) | 3.50744 | 3.47 | 46.07(1) | 1.96877 | 2.02 |
| 25.772(1) | 3.45406 | 22.32 | 46.96(1) | 1.93317 | 2.00 |
| 26.090(4) | 3.41271 | 4.48 | 51.307(8) | 1.77926 | 1.65 |
| 26.407(4) | 3.37239 | 4.46 | 52.797(7) | 1.73251 | 1.15 |
| 26.793(1) | 3.32478 | 13.11 | | | |

2. Differential Scanning Calorimetry Analysis (DSC)

DSC analysis was performed by using a seal disc device on a TA Instruments™ Q2000. The sample (about 1 to 3 mg) was weighed in an aluminium pan with a Tzero gland, and the weight was recorded accurately to 0.01 mg, and the sample was transferred to the instrument for measurement. The instrument was purged with nitrogen at 50 mL/min. The data were collected at a heating rate of 10° C./min from room temperature to 300° C. The curve was drawn and the downward peak was endothermic peak in the curve, and the data were analyzed and displayed by TA Universal Analysis software.

FIG. 2 shows a DSC thermogram of crystalline Form I of Compound (I). The figure shows that the DSC thermogram comprises an endothermic peak at 91.55° C., which may have an error margin of ±2° C.

FIG. 5 shows a DSC thermogram of crystalline Form II of Compound (I). The figure shows that the DSC thermogram comprises an endothermic peak at 80.53° C., which may have an error margin of ±2° C.

3. Thermogravimetric Analysis (TGA)

Detection of TGA was performed on a TA Instruments™ Q500. The procedure comprised removing tare weight of an empty crucible, taking about 10 mg solid sample and paving evenly in the empty crucible, The data were collected at a heating rate of 10° C./min from room temperature to 300° C. under nitrogen purge after the instrument run stably, and a thermogram was recorded.

FIG. 3 shows a TGA thermogram of crystalline Form I of Compound (I). The figure shows a weight loss of about 0.21% at 150° C.

FIG. 6 shows a TGA thermogram of crystalline Form II of Compound (I). The figure shows a weight loss of about 2.16% at 150° C.

4. Single Crystal X-Ray Diffraction

Crystalline Form I was analyzed by single crystal X-ray diffraction using Gemini Ultra single-crystal X-ray diffractometer. The initial lattice parameters were obtained by CrysAlisPro program. The diffraction data were collected according to the method recommended by the instrument. The collected data were restored and absorbed by CrysAlisPro program, and the unit cell parameters were refined. The initial structure was obtained by SHELXTL program, followed by the whole matrix least squares method to refine the structure. Finally, a crystallographic data sheet was obtained using the SHELXTL program. The cell unit parameters are shown in Table 4.

TABLE 4

| Crystalline Form I Unit Cell Parameters | |
|---|---|
| Crystal system | Triclinic |
| Space group | P-1 |
| a (Å) | 12.501 |
| b (Å) | 12.853 |
| c (Å) | 13.235 |
| α (°) | 77.555 |
| β (°) | 70.404 |
| γ (°) | 70.239 |

5. Stability

Samples of a mixture of crystalline Form I and Form II of Compound (I) were added to water at room temperature or 60° C. to form suspensions, which were stirred for 24 hours, and solids were analyzed by X-ray diffraction. The results show that the mixture remained as a mixture of crystalline Form I and Form II after stirring for 24 hours at room temperature, but completely converted to crystalline Form I at 60° C. Crystalline Form II also converted to Form I upon long term storage at room temperature.

Thin layers (≤5 mm) of crystalline Form I were placed under high temperature (60±2° C.), high humidity (92.5%±2% humidity), light (visible light 4500 lx±500 lx) and ambient temperature (25±2° C., 65%±5% humidity) for 15 days, and samples were analyzed by HPLC on day 5, 9 and 15. The results of the percentage of impurity in the samples are shown in Table 5. As indicated in Table 5, crystalline Form I did not exhibit significant chemical change.

TABLE 5

| Days | 0 | 5 | 10 | 15 |
|---|---|---|---|---|
| 60 ± 2° C. | 0.04% | 0.04% | 0.02% | 0.02% |
| 92.5% ± 2% humidity | 0.04% | 0.06% | 0.06% | 0.02% |
| Visible light | 0.04% | 0.03% | 0.03% | 0.02% |
| Ambient temperature | 0.04% | 0.04% | 0.04% | 0.01% |

6. Hygroscopicity

Samples of crystalline Form I in weighing bottles exhibited weight gains of 0.03% and 0.06% when placed in containers containing saturated $NH_4Cl$ aqueous solution (80%±2% RH) or saturated $KNO_3$ aqueous solution (92.5%±2% RH), respectively, at 25° C.±1° C. for 24 hours, indicating lack of hygroscopicity.

We claim:

1. A crystalline form of Compound (I)

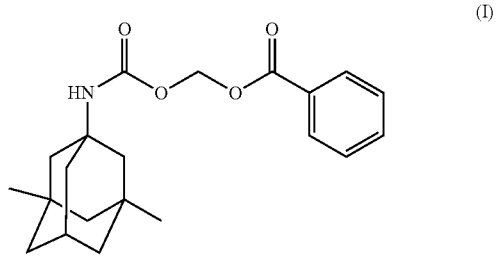 [SMILES: CC12CC3CC(C)(C1)CC(NC(=O)OCOC(=O)c1ccccc1)(C3)C2]

(I)

selected from crystalline Form I characterized by an X-ray powder diffraction pattern comprising at least three peaks selected from the peaks expressed as 2θ at 7.7±0.2°, 8.9±0.2°, 10.7±0.2°, 13.1±0.2°, 14.2±0.2°, 15.4±0.2°, 18.0±0.2°, 18.7±0.2°, 21.4±0.2°, 21.6±0.2°, 22.4±0.2°, 22.8±0.2°, 23.9±0.2°, 25.5±0.2°, 26.5±0.2°, and 27.0±0.2°, or crystalline Form II characterized by an X-ray powder diffraction pattern comprising at least three peaks selected from the peaks expressed as 2θ at 9.6±0.2°, 13.8±0.2°, 14.7±0.2°, 15.0±0.2°, 16.1±0.2°, 16.8±0.2°, 17.8±0.2°, 18.5±0.2°, 19.0±0.2°, 19.4±0.2°, 20.4±0.2°, 21.7±0.2° and 22.6±0.2°.

2. The crystalline form of Compound (I) according to claim 1, wherein the crystalline form exists in substantially anhydrous form.

3. The crystalline form of Compound (I) according to claim 1, wherein the crystalline form is crystalline Form I characterized by an X-ray powder diffraction pattern comprising at least one group of peaks expressed as 2θ selected from the groups consisting of: (A) 7.7±0.2°, 8.9±0.2°, and 10.7±0.2°; (B) 13.1±0.2°, 15.4±0.2°, and 18.0±0.2°; (C) 21.6±0.2°, 22.8±0.2°, and 23.9±0.2°; and (D) 25.5±0.2°, 26.5±0.2°, and 27.0±0.2°.

4. The crystalline form of Compound (I) according to claim 1, wherein the crystalline form is crystalline Form I characterized an X-ray powder diffraction pattern comprising peaks expressed as 2θ at 14.2±0.2°, 15.4±0.2°, 18.0±0.2°, and 18.7±0.2°.

5. The crystalline form of Compound (I) according to claim 1, wherein the crystalline form is crystalline Form I characterized by an X-ray powder diffraction pattern comprising peaks expressed as 2θ at 14.2±0.2°, 15.4±0.2°, 18.0±0.2°, 18.7±0.2°, 21.4±0.2°, 21.6±0.2° and 22.4±0.2°.

6. The crystalline form of Compound (I) according to claim 1, wherein the crystalline form is crystalline Form I characterized by an X-ray powder diffraction pattern comprising peaks expressed as 2θ at 7.7±0.2°, 8.9±0.2°, 14.2±0.2°, 15.4±0.2°, 16.7±0.2°, 17.7±0.2°, 18.0±0.2°, 18.7±0.2°, 19.2±0.2°, 21.4±0.2°, 21.6±0.2°, 22.4±0.2°, and 22.8±0.2°.

7. The crystalline form of Compound (I) according to claim 1, wherein the crystalline form is crystalline Form I characterized by a differential scanning calorimetry thermogram comprising an endothermic peak at 91.55° C.±2° C.

8. The crystalline form of Compound (I) according to claim 1, wherein the crystalline form is crystalline Form II characterized by an X-ray powder diffraction pattern comprising at least one group of peaks expressed as 2θ selected from the groups consisting of: (A) 9.6±0.2°, 13.8±0.2°, and 14.7±0.2°; (B) 15.0±0.2°, 16.1±0.2°, and 16.8±0.2°; (C) 17.8±0.2°, 18.5±0.2°, and 19.0±0.2°; and (D) 19.4±0.2°, 20.4±0.2°, and 21.7±0.2°.

9. The crystalline form of Compound (I) according to claim 1, wherein the crystalline form is crystalline Form II characterized by an X-ray powder diffraction pattern comprising peaks expressed as 2θ at 13.8±0.2°, 14.7±0.2°, 15.0±0.2°, 16.1±0.2°, 16.8±0.2°, 18.5±0.2°, 19.4±0.2°, 21.7±0.2° and 22.6±0.2°.

10. The crystalline form of Compound (I) according to claim 1, wherein the crystalline form is crystalline Form II characterized by an X-ray powder diffraction pattern comprising peaks expressed as 2θ at 13.8±0.1°, 14.7±0.1°, 15.0±0.1°, 16.1±0.1°, 16.8±0.1°, 18.5±0.1°, 19.4±0.1°, 21.7±0.1° and 22.6±0.1°.

11. The crystalline form of Compound (I) according to claim 1, wherein the crystalline form is crystalline Form II characterized by an X-ray powder diffraction pattern comprising peaks expressed as 2θ at 9.6±0.2°, 13.8±0.2°, 14.7±0.2°, 15.0±0.2°, 16.1±0.2°, 16.8±0.2°, 17.8±0.2°, 18.5±0.2°, 19.0±0.2°, 19.4±0.2°, 20.4±0.2°, 21.7±0.2°, 22.6±0.2°, 23.2±0.2°, and 24.5±0.2°.

12. The crystalline form of Compound (I) according to claim 1, wherein the crystalline form is crystalline Form II characterized by a differential scanning calorimetry thermogram comprising an endothermic peak at 80.53° C.±2° C.

13. A pharmaceutical composition comprising crystalline Form I or II of Compound (I) according to claim 1 or a combination thereof, and a pharmaceutically acceptable excipient.

14. The pharmaceutical composition according to claim 13, wherein the pharmaceutical composition further comprises a cholinesterase inhibitor.

15. The pharmaceutical composition according to claim 14, wherein the cholinesterase inhibitor is tacrine, donepezil, huperzine-A, galanthamine, or rivastigmine, or a combination thereof.

16. A method for treating Alzheimer's disease in a subject in need thereof, comprising administering to the subject the crystalline form according to claim 1.

17. The method of claim 16 further comprising administering to the subject a cholinesterase inhibitor.

18. The method of claim 17, wherein the cholinesterase inhibitor is tacrine, donepezil, huperzine-A, galanthamine, or rivastigmine, or a combination thereof.

* * * * *